United States Patent
Sundararajan et al.

(10) Patent No.: US 7,835,801 B1
(45) Date of Patent: Nov. 16, 2010

(54) ELECTRIC LEAD WITH CONTROLLABLE FIXATION

(75) Inventors: Jay Sundararajan, Minnetonka, MN (US); Ali Dianaty, Northridge, CA (US); Yougandh Chitre, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 434 days.

(21) Appl. No.: 11/674,541

(22) Filed: Feb. 13, 2007

(51) Int. Cl.
*A61N 1/00* (2006.01)

(52) U.S. Cl. .................................................. 607/119

(58) Field of Classification Search .............. 607/126, 607/119
See application file for complete search history.

(56) References Cited

U.S. PATENT DOCUMENTS

| | | | |
|---|---|---|---|
| 4,913,164 A * | 4/1990 | Greene et al. | 607/126 |
| 5,217,028 A * | 6/1993 | Dutcher et al. | 607/120 |
| 6,198,973 B1 | 3/2001 | Doan et al. | |
| 6,430,448 B1 | 8/2002 | Chitre et al. | |
| 6,766,203 B2 | 7/2004 | Doan et al. | |
| 6,792,318 B2 | 9/2004 | Chitre et al. | |
| 6,973,352 B1 | 12/2005 | Tsutsui et al. | |
| 7,058,454 B1 | 6/2006 | Chitre et al. | |
| 2004/0147976 A1* | 7/2004 | Gordon et al. | 607/48 |
| 2005/0131509 A1* | 6/2005 | Atanassoska et al. | 607/122 |
| 2006/0015164 A1* | 1/2006 | Partridge et al. | 607/119 |

* cited by examiner

*Primary Examiner*—Niketa I Patel
*Assistant Examiner*—Shubatra Narayanaswamy

(57) ABSTRACT

Embodiments include electrical leads and methods of using electrical leads that may be implantable and are controllably secured to target tissue. Some embodiments may include radially extending tissue engaging members that may serve as electrodes and which may be retracted if necessary to remove embodiments of an electrical lead.

16 Claims, 20 Drawing Sheets

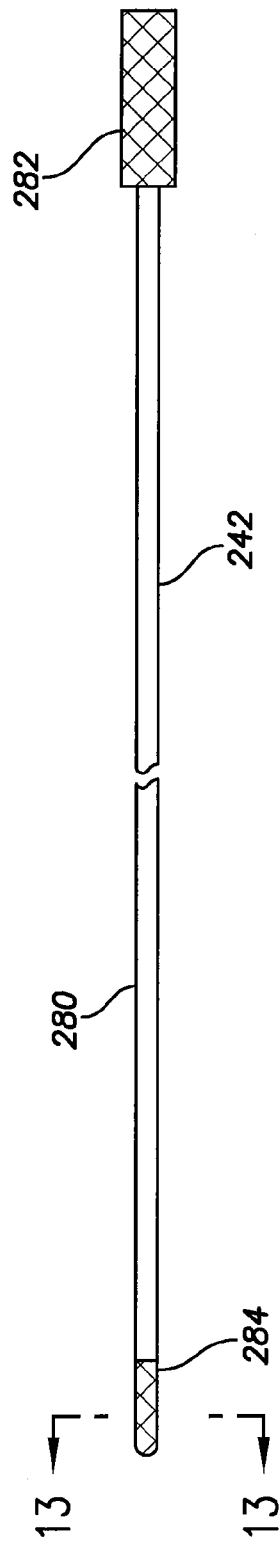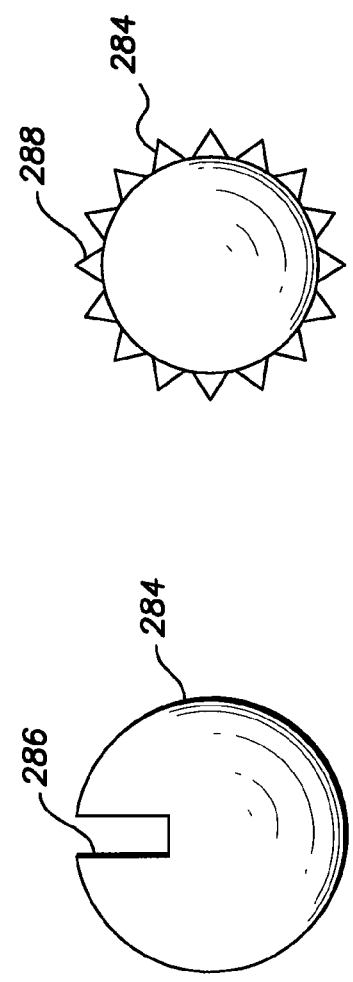

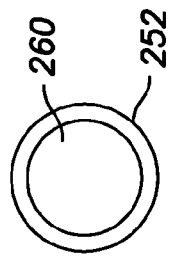
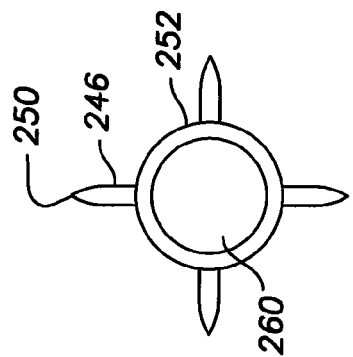
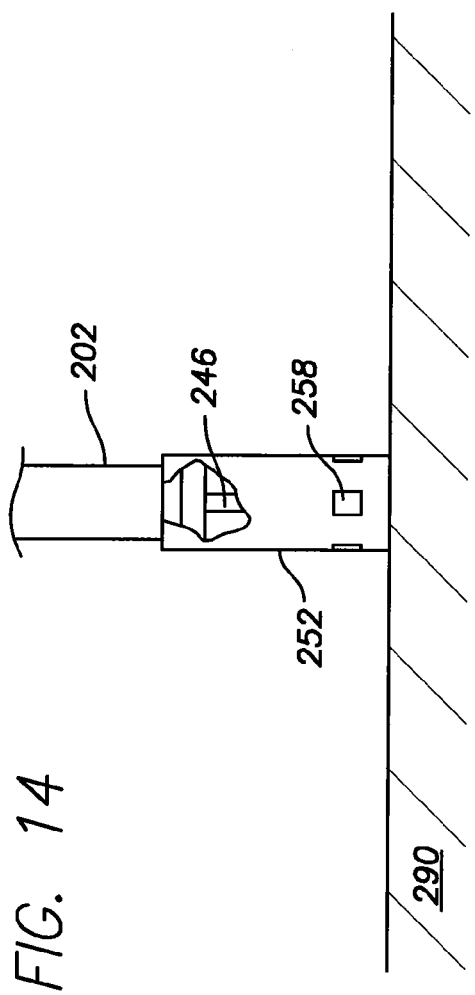
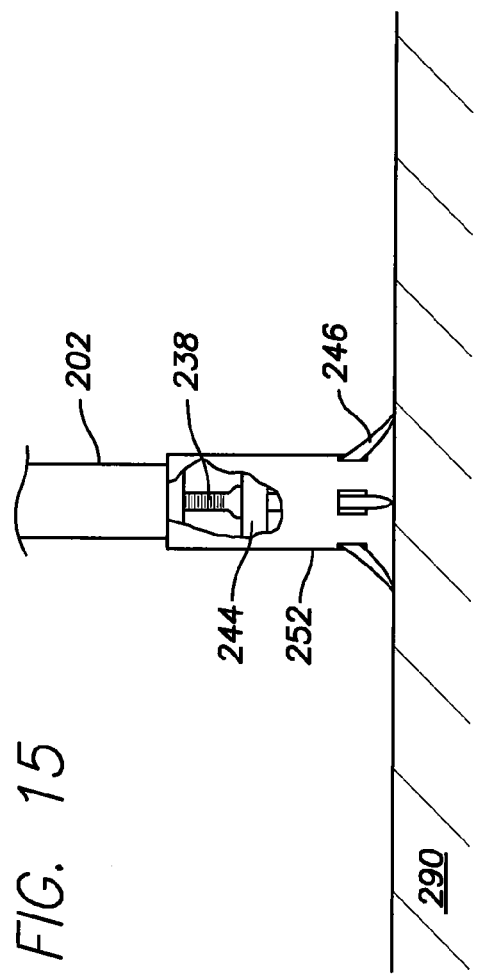

FIG. 22
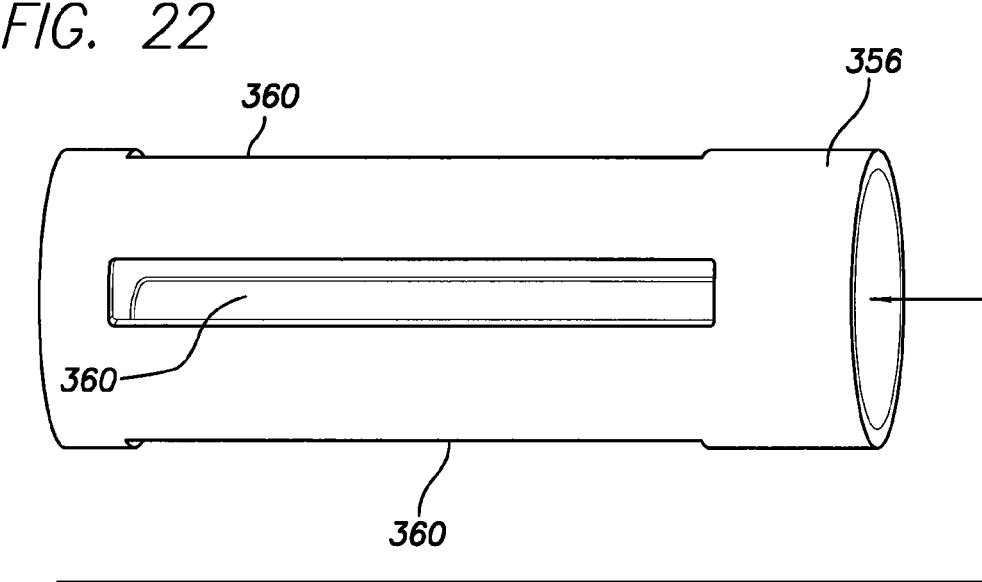
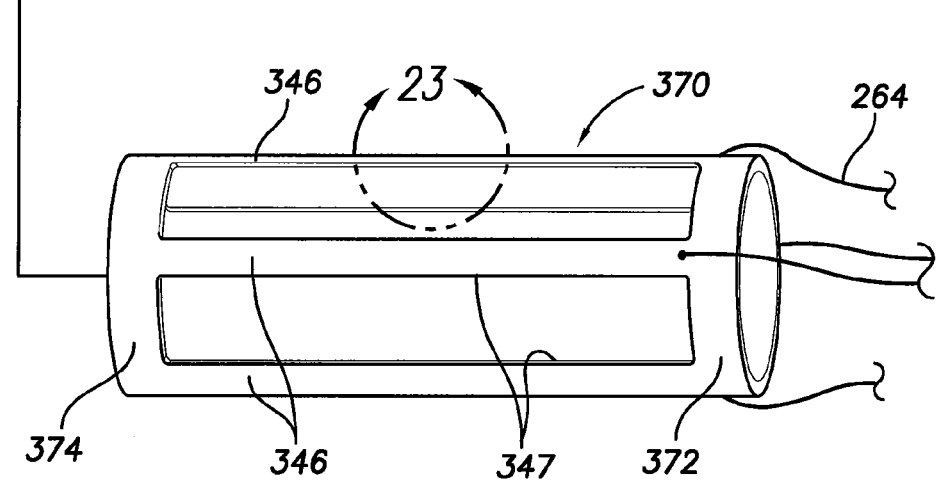
FIG. 23
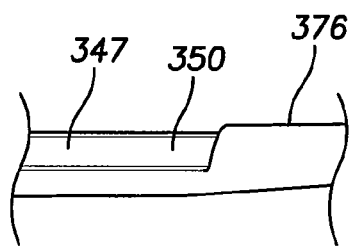

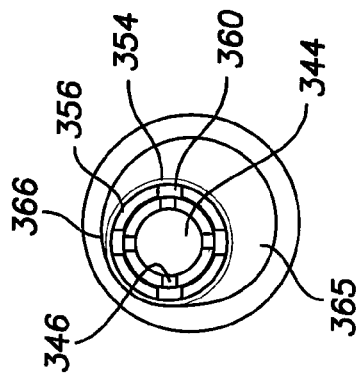
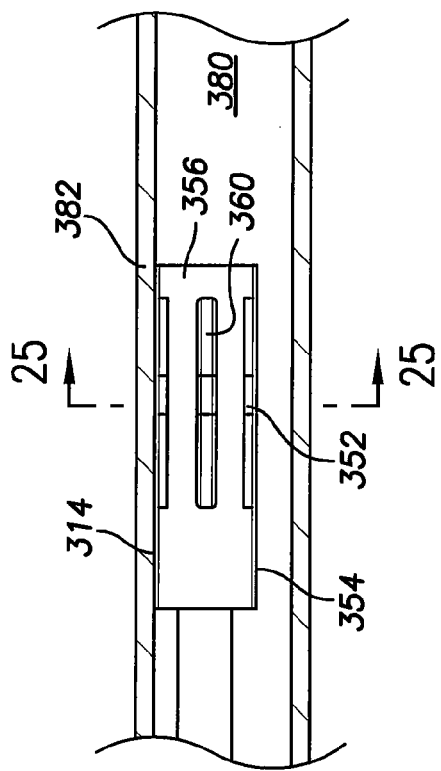
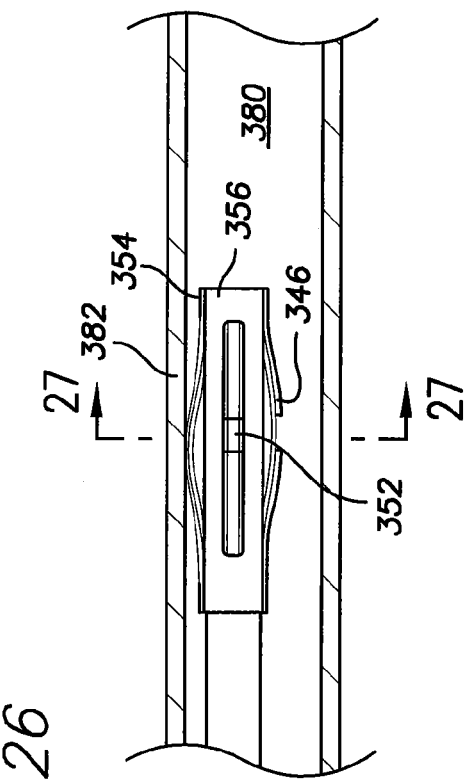

ELECTRIC LEAD WITH CONTROLLABLE FIXATION

FIELD OF THE INVENTION

Embodiments of the present invention generally relate to implantable medical devices such as implantable electrical stimulation devices including pacemakers, implantable cardioverter/defibrillators (ICDs) and the like. In particular, embodiments of the invention are directed to electrical leads that couple output signals of stimulation devices such as ICDs and the like to target tissue to be stimulated.

BACKGROUND

Body implantable electrical leads form the electrical connection between stimulation devices, such as a cardiac pacemaker, and target body tissue, such as that of the heart, which is to be electrically stimulated. As is well known, the leads connecting pacemakers with the heart may be used for pacing or for sensing electrical signals produced by the heart, or for both pacing and sensing in which case a single electrical lead serves as a bi-directional pulse transmission link between the pacemaker and the heart. An endocardial electrical lead which is inserted into a vein and guided therethrough into a cavity or chamber of the heart, includes at its distal tip an electrode designed to contact the endocardium. Such an electrical lead further includes a proximal end carrying an electrical connector assembly adapted to be received by a receptacle in the pacemaker. A flexible cable or coil conductor surrounded by an insulating sheath couples a terminal contact on the electrical connector assembly with the electrode at the distal tip.

To prevent displacement or dislodgment of the tip electrode and to maintain the necessary stable electrical contact between the tip electrode and the endocardial tissue, the electrode must be firmly anchored relative to the tissue. To achieve this, one type of lead, sometimes referred to as an active fixation lead, includes a pointed, extendable/retractable helix adapted to be screwed into the heart tissue to be stimulated. In this fashion, the position of the tip electrode is mechanically stabilized by positively anchoring the lead tip so that it remains securely in place during the lifetime of the implant.

The fixation helix may itself comprise the tip electrode in which case it is electrically coupled by means of a coil conductor to a rotatable terminal contact pin on the connector assembly. Rotational torque applied to the connector pin at the proximal end of the lead is transmitted via the coil conductor to the helix electrode which is thereby screwed into the heart tissue. Removal of the screw-in electrode from the endocardium is effected by counter-rotation of the connector pin. Thus, in electrical leads having a screw-in helix electrode, the coil conductor is used not only as a conductor for electrically coupling the connector pin and the helix electrode, but also as a tool for extending or retracting the helix electrode relative to the distal end of the lead during lead fixation or removal by rotating the connector pin.

Such conventional electrical leads are an important element of implantable cardiac stimulation devices and the like. Current electrical lead designs are adequate in many respects, however, they can be difficult to remove and often do not provide sufficient surface area contact of the electrodes. In particular, the area of tissue engaged by a helix electrode is limited by the outer diameter of the lead header. In addition, the helix electrode is limited to a single point of tissue contact for electrical stimulation. What has been needed are electrical leads for electrical stimulation devices and the like that are easy to deploy, reliably and controllably secured to target tissue and readily removed from target tissue if necessary. What has also been needed is electrical leads that may be used to provide multiple tissue contact points for electrical stimulation signal delivery upon deployment.

SUMMARY

Some embodiments of an implantable electrical lead include an elongate flexible lead body having a distal portion and a plurality of substantially axially coextensive resilient tissue engaging members disposed at the distal portion of the lead body. The tissue engaging members are configured to be controllably expandable from a retracted state to a radially extended state so as to engage adjacent target tissue. An axial displacement mechanism is mechanically coupled to the tissue engaging members in order to control the radial extension. At least one electrode is disposed at the distal portion of the lead body and a connector having one or more conductive terminals is disposed at a proximal end of the lead body. At least one conductor cable is in electrical communication between respective electrode or electrodes and conductive terminals of the connector.

Some embodiments of an implantable electrical lead include an elongate flexible lead body and an axial displacement mechanism disposed at a distal portion of the flexible lead body. A plurality of resilient tissue engaging members are disposed at the distal end of the lead body. Each tissue engaging member has a sharpened distal end configured to penetrate target tissue and an electrode. The resilient tissue engaging members are oriented in an axial direction substantially axially coextensive with each other while in a radially retracted state and configured to be radially extended in a controllable manner from the radially retracted state to a radially extended state. In the radially extended state, the sharpened distal ends extend radially outwardly and distally from the lead body so as to engage target tissue disposed adjacent to and distal of the distal end of the lead body. A tubular header is disposed at the distal end of the lead body which constrains the tissue engaging members while they are in the radially retracted state. The header also has a plurality of radially oriented apertures corresponding to each resilient tissue engaging member configured to allow each respective tissue engaging member to extend from the radially oriented aperture upon deployment of the tissue engaging member from the radially constrained state. A connector is disposed at a proximal end of the lead body and has a plurality of conductive terminals. Conductor cables are in electrical communication between respective electrodes and conductive terminals of the connector.

Some embodiments of an implantable electrical lead include an elongate flexible lead body and an axial displacement mechanism disposed at a distal portion of the flexible lead body. A plurality of resilient tissue engaging members is disposed at the distal portion of the shaft and configured to be radially extended in a controllable manner from a radially retracted state to a radially extended state. A proximal end and distal end of each tissue engaging member is radially constrained but the proximal end and distal end of each tissue engaging member are axially moveable relative to each other. The tissue engaging members are straight and substantially aligned in an axial orientation in the radially retracted state. An intermediate portion of each tissue engaging member disposed between the proximal end and distal end includes an electrode. The intermediate portion of each tissue engaging member is deflected radially outward upon deployment by moving the respective proximal end and distal end closer together axially. A header has a side wall disposed about an inner lumen of the header and an elongate aperture corresponding and disposed radially adjacent to each tissue engaging member. The intermediate portion of each tissue engaging member extends in a radial direction beyond the header through each respective elongate aperture when the tissue engaging members are in a deployed state. A connector is disposed at a proximal end of the shaft and has a plurality of conductive terminals. Conductor cables are in electrical communication between respective electrodes and conductive terminals of the connector.

Some methods of deploying an implantable electrical lead include advancing an implantable electrical lead within a patient's body until a distal portion of the electrical lead is disposed adjacent target tissue of the patient's body. A plurality of tissue engaging members are then controllably deployed from the distal portion of the electrical lead from a retracted state to a radially extended state to as to engage the target tissue and secure the distal portion of the electrical lead to the target tissue. An electrical signal is then conducted through an electrode on the distal portion of the implantable electrical lead.

These features of embodiments will become more apparent from the following detailed description when taken in conjunction with the accompanying exemplary drawings.

BRIEF DESCRIPTION OF THE DRAWINGS

FIG. 12 is an elevational view of a stylet configured to engage a coupling portion of a screw member of the electrical lead of FIG. 4.

FIG. 13A shows a transverse cross sectional view of a distal portion of the stylet of FIG. 12 taken along lines 13-13 illustrating a slotted torque transferring embodiment.

FIG. 13B shows a transverse cross sectional view of a distal portion of the stylet of FIG. 12 taken along lines 13-13 illustrating a splined torque transferring embodiment.

FIG. 13C shows a transverse cross sectional view of a distal portion of the stylet of FIG. 12 taken along lines 13-13 illustrating a threaded torque transferring embodiment.

FIG. 14 is a side view of a distal portion of the electrical lead of FIG. 4 with the distal end of the header disposed in contact with target tissue of a patient and the tissue engaging members in a retracted state.

FIG. 14A is an end view of the electrical lead of FIG. 14 with the tissue engaging members in a retracted state.

FIG. 15 is a side view of the distal portion of the electrical lead of FIG. 14 with the tissue engaging members in a partially radially extended state and the sharpened distal ends of the tissue engaging members advanced radially outward and distally forward so as to contact the target tissue.

FIG. 15A is an end view of the electrical lead of FIG. 15 with the tissue engaging members in a partially radially extended state.

FIG. 22 is an exploded view of a portion of a header assembly embodiment.

FIG. 23 is an enlarged view of a portion of the tissue engaging member embodiment shown in FIG. 22 and indicated by the encircled portion 23-23 in FIG. 22.

FIG. 24 is an elevational view of a distal portion of an electrical lead embodiment disposed within a body lumen of a patient prior to deployment with the tissue engaging members in a retracted state.

FIG. 25 is a transverse cross sectional view of the body lumen and electrical lead of FIG. 24 taken along lines 25-25 of FIG. 24.

FIG. 26 shows the electric lead of FIG. 24 with the tissue engaging members of the electrical lead in a partially radially extended state within the body lumen.

FIG. 27 is a transverse cross sectional view of the electrical lead of FIG. 26 taken along lines 27-27 of FIG. 26.

DETAILED DESCRIPTION

Embodiments discussed herein relate to cardiac pacing methods, cardiac sensing methods and associated devices designed to relieve a variety of conditions that result from cardiac disease as well as other conditions. In order to pace or otherwise impart electrically delivered therapy to a patient's tissue, such as heart tissue, an electrical lead or delivery system is typically required. An electrical lead is used to deliver a therapeutic signal from a stimulation device to a target tissue site of the patient's body. Following is a general discussion of stimulation device embodiments that may be used with electric lead and stimulation method embodiments discussed herein.

Overview of Stimulation Device Embodiments

Figure 1:
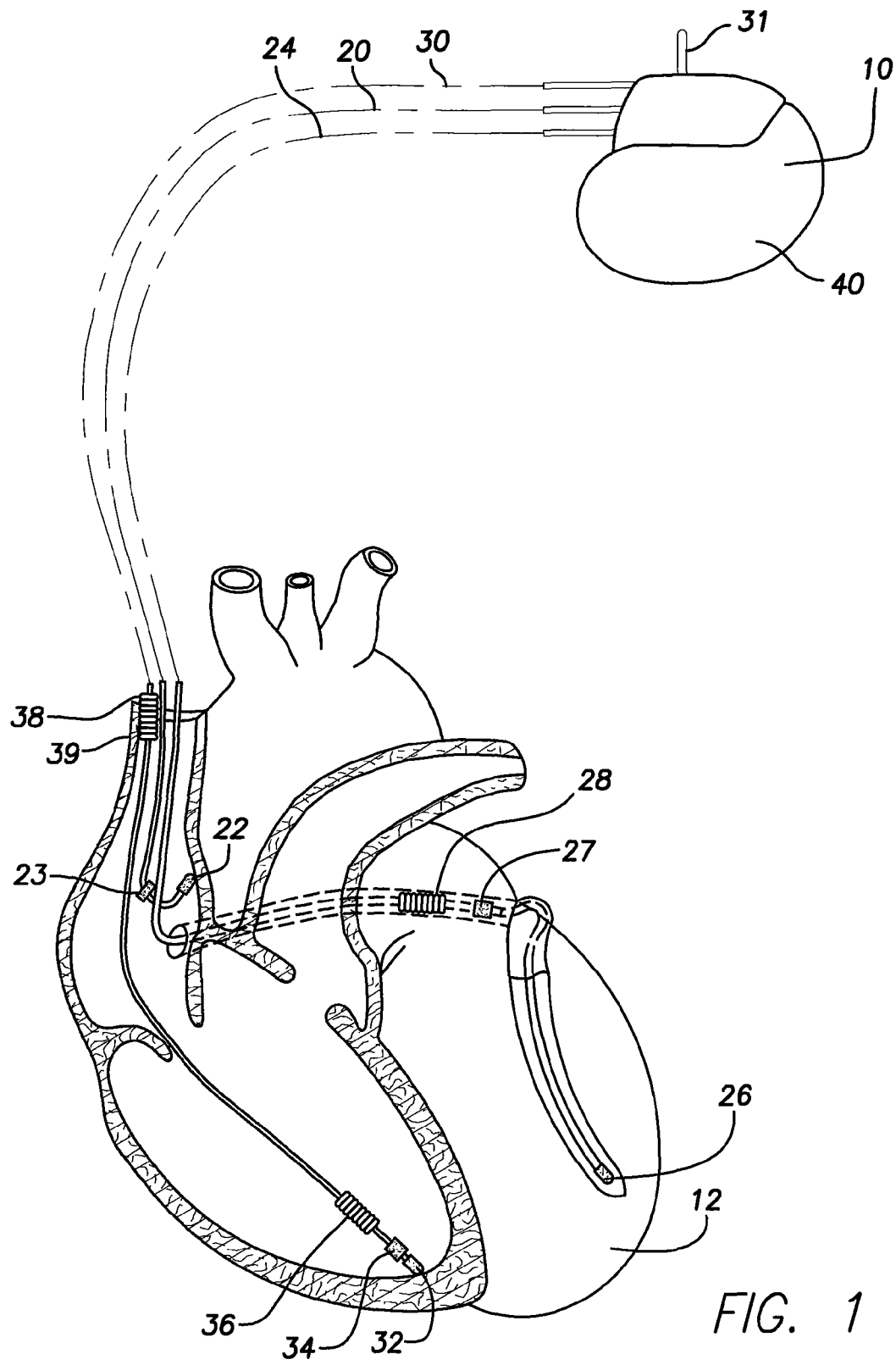
FIG. 1 is a simplified diagram illustrating an implantable cardiac stimulation device in electrical communication with at least three electrical leads implanted into the heart of a patient.

FIG. 1 shows a stimulation device 10 in electrical communication with the heart 12 of a patient with three electrical leads, 20, 24 and 30, in a configuration suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode is positioned in the right ventricle and the SVC coil electrode 38 is positioned in the superior vena cava 39. Accordingly, the right ventricular lead 30 is capable of receiving cardiac signals, and delivering stimulation in the form of pacing and shock therapy to the right ventricle. The stimulation device 10 includes an outer housing 40 that may be electrically conductive.

Figure 2:
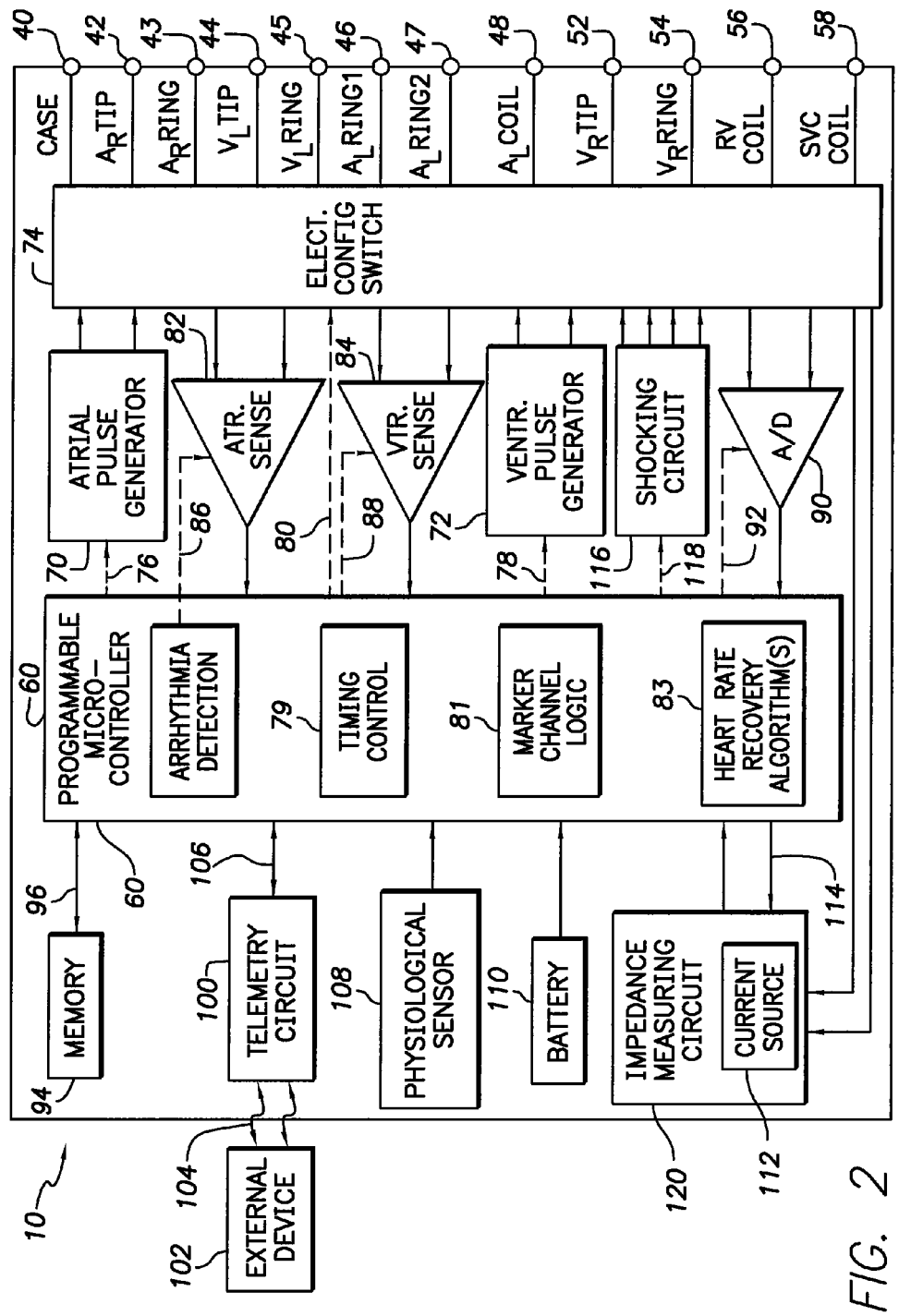
FIG. 2 is a functional block diagram of a multi-chamber implantable stimulation device illustrating exemplary basic elements of a stimulation device which can provide cardioversion, defibrillation, and/or pacing stimulation in up to four chambers of the heart.

As illustrated in FIG. 2, a simplified block diagram is shown of the multi-chamber implantable cardiac stimulation device 10, which is capable of treating both fast and slow arrhythmias with stimulation therapy, including cardioversion, defibrillation, and pacing stimulation. While a particular multi-chamber device is shown, this is for illustration purposes only, and appropriate circuitry may be duplicated, eliminated or disabled in any desired combination to provide a device capable of treating the appropriate chamber(s) with cardioversion, defibrillation and pacing stimulation. In addition, some processing step embodiments discussed below may be implemented in the form of software instructions that are resident on a computer-readable media that is included with the stimulation device 10.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 45, 46, 47, 48, 52, 54, 56 and 58 (shown schematically and, for convenience, the names of the electrodes to which they are connected are shown next to the terminals). While it is recognized that the number of terminals of current devices may be limited due to international standards, some terminals/electrodes may be programmably eliminated/selected in order to accommodate various embodiments. In addition, standards may change in the future and accommodate additional configurations.

To achieve right atrial sensing and pacing, the connector includes at least a right atrial tip terminal ($A_R$ TIP) 42 and a right atrial ring terminal ($A_R$ RING) 43, adapted for connection to the atrial tip electrode 22 and atrial ring electrode 23, respectively. To achieve left chamber sensing, pacing and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a controller in the form of a programmable microcontroller 60, which controls the various modes of stimulation therapy. The microcontroller 60 (also referred to herein as a controller or control unit) includes a microprocessor, or equivalent control circuitry, designed specifically for detecting sensed cardiac function data, generating warning signals that may be felt, heard or seen by a patient, controlling delivery of stimulation therapy as well as other function and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein. Microprocessor-based control circuits for performing timing and data analysis functions may be used.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. In order to provide stimulation therapy in each of the four chambers of the heart 12, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 also includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, blanking intervals, noise detection windows, evoked response windows, alert intervals, marker channel timing (via marker channel logic 81), etc. Some embodiments of the microcontroller 60 are programmed with one or more heart rate recovery algorithms 83. The heart rate recovery algorithm(s) operate to monitor a patient's heart rate recovery when, for example, the patient recovers from a period of exercise to a period of rest. The algorithms can then save data associated with the heart rate recovery.

Switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, combipolar, etc.) and various shocking vectors by selectively closing the appropriate combination of switches (not shown). Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart 12. The atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches. In this way, the clinician may program the sensing polarity independent of the stimulation polarity.

Each sensing circuit, 82 and 84, preferably employs one or more low power, precision amplifiers with programmable gain and/or automatic gain control, band pass filtering, and a threshold detection circuit to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart 12.

For arrhythmia detection, the stimulation device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia or other clinical condition. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). The atrial and ventricular sensing circuits 82 and 84 receive control signals over signal lines 86 and 88 from the microcontroller 60, for controlling gain, threshold, polarization charge removal circuitry, and the timing of any blocking circuitry coupled to the inputs of the atrial and ventricular sensing circuits 82 and 84.

Cardiac signals may also be applied to the inputs of an analog-to-digital (A/D) data acquisition system 90. The data acquisition system 90 may be configured to acquire intracardiac electrogram signals, convert the raw analog data into a digital signal, and store the digital signals for later processing and/or telemetric transmission to an external device 102. The microcontroller 60 enables the data acquisition system 90 via control signal 92 to sample the cardiac signal that falls within a capture detection window. The data acquisition system 90 is coupled to the right atrial lead 20, the coronary sinus lead 24, and the right ventricular lead 30 through the switch 74 to sample cardiac signals across any pair of desired electrodes. The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

The operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 allows intracardiac electrograms and status information relating to the operation of the device 10 (as contained in the microcontroller 60 or memory 94) to be sent to the external device 102 through an established communication link 104.

In some embodiments, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart 12, or diurnal changes in activity (e.g., detecting sleep and wake states). A physiological parameter of the heart 12, which may be measured to optimize such pacing and to indicate when such pacing may be inhibited or terminated is the stroke volume of the heart 12. Accordingly, the microcontroller 60 responds by adjusting the various pacing parameters (such as rate, AV Delay, V-V Delay, etc.) at which the atrial and ventricular pulse generators, 70 and 72, generate stimulation pulses. A common type of rate responsive sensor is an activity sensor, such as an accelerometer or a piezoelectric crystal, which is mounted within the housing 40 of the stimulation device 10. While shown as being included within the stimulation device 10, the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may use lithium/silver vanadium oxide batteries.

In the case where the stimulation device 10 is intended to operate as an implantable cardioverter/defibrillator (ICD) device, it detects the occurrence of an arrhythmia and automatically applies an appropriate electrical shock therapy to the heart 12 aimed at terminating the detected arrhythmia. The microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38, as shown in FIG. 1. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the device 10 is shown as having an impedance measuring circuit 120 including an impedance measuring current source 112 and a voltage measuring circuit 90 (shown in FIG. 2 as an A/D converter), which may be enabled by the microcontroller 60 via a control signal 114 for providing stroke volume measurements of the heart 12. The current source 112 can provide an alternating or pulsed excitation current. The voltage measuring circuitry 90 may also take the form of, for example, a differential amplifier. The uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring a respiration parameter (for example, tidal volume, respiration rate, minute ventilation or volume, abnormal or periodic breathing); measuring thoracic impedance for determining shock thresholds and shock timing (corresponding to the diastolic time); detecting when the device has been implanted; measuring a cardiac parameter (such as, stroke volume, wall thickness, left ventricular volume, etc.); and detecting the opening of the valves etc.

Electrical Lead Embodiments

Figure 3:
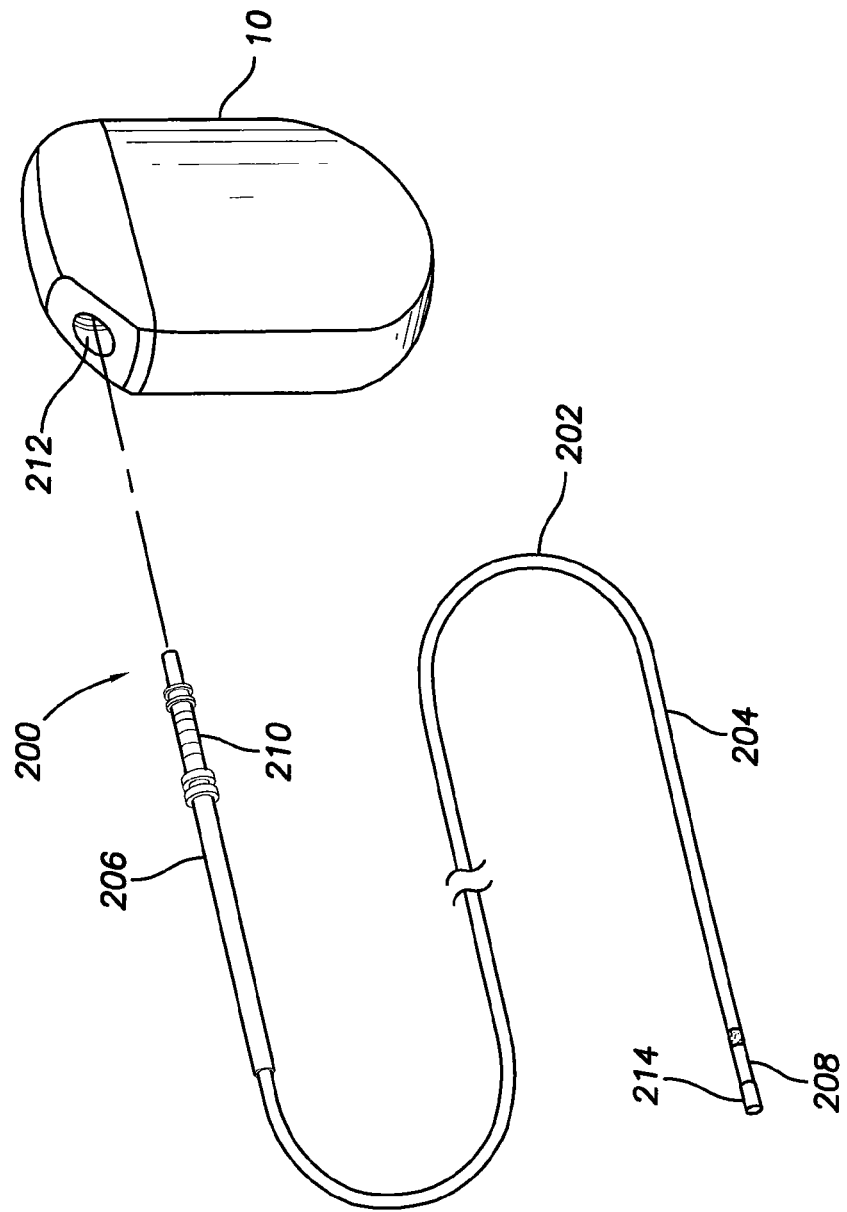
FIG. 3 is an exploded perspective view of an embodiment of a system for delivering therapeutic electric signals to tissue of a patient.

The general discussion of the stimulation device 10 above has been made with reference to various electrical leads having a substantially conventional configuration. However, in some cases, it may be desirable to have an electrical lead with a controllable fixation mechanism that extends axially from a distal portion of an electrical lead. FIG. 3 illustrates a system 200 for delivering electrical stimulation energy to target tissue a patient including stimulation device 10 and an electrical lead 202 having an elongate flexible lead body 204 with a proximal end 206 and distal end 208. A connector 210 is disposed on the proximal end of the lead body 204 and is configured to be sealingly and electrically coupled to a receptacle 212 of the stimulation device 10. A header assembly 214 is disposed on the distal end 208 of the lead body 204.

Figure 4:
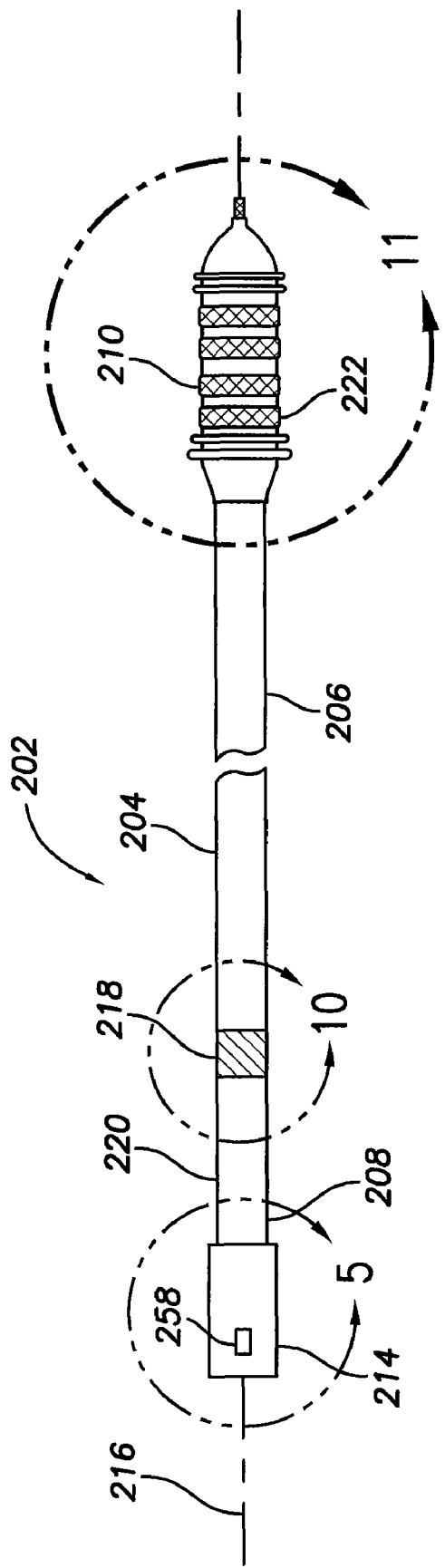
FIG. 4 is an elevational view of an embodiment of an electrical lead.
Figure 5:
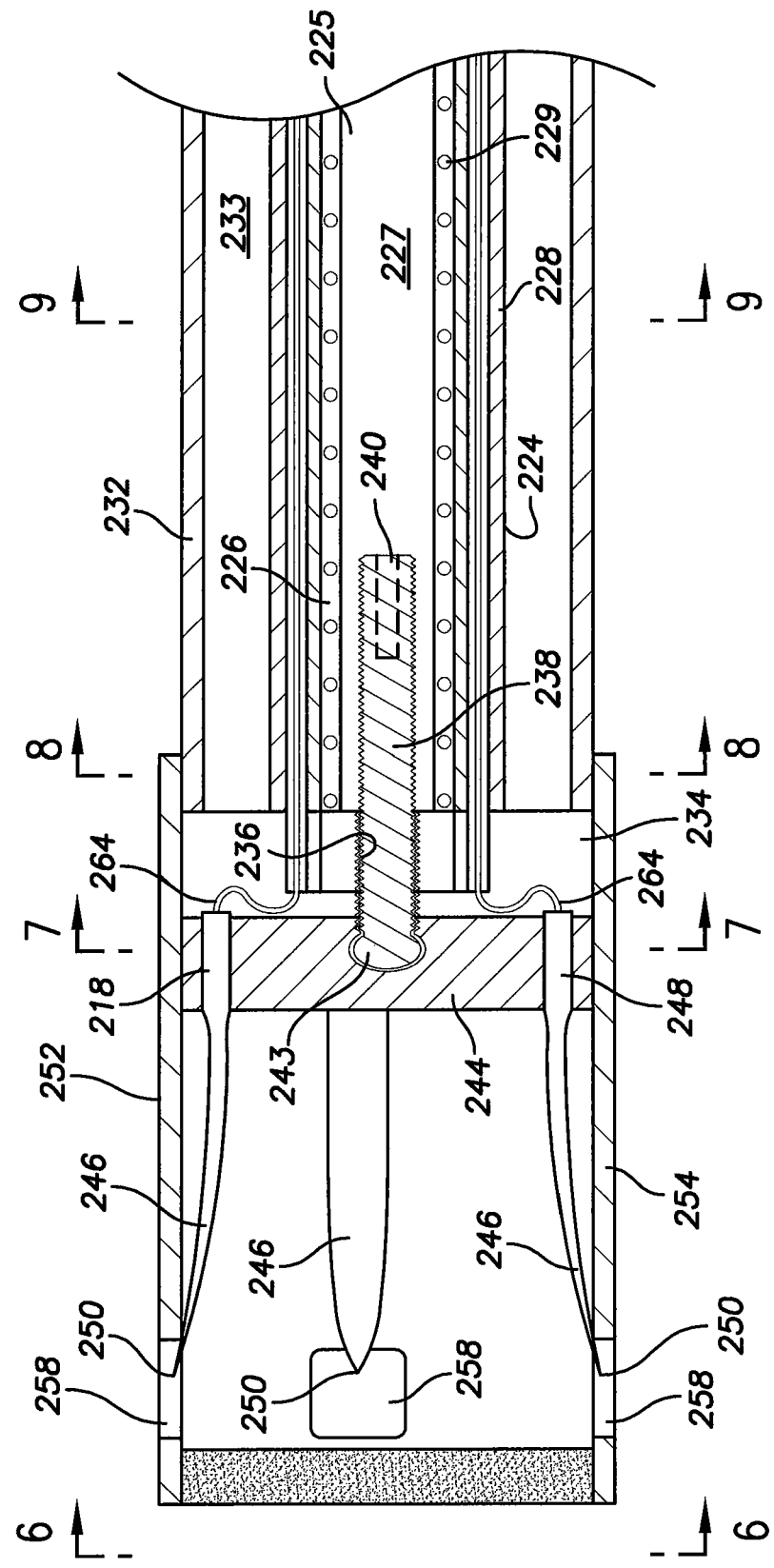
FIG. 5 is an enlarged view of the encircled portion 5-5 of FIG. 4.
Figure 6:
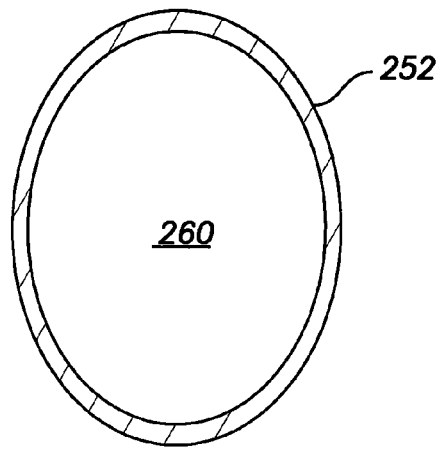
FIG. 6 is a transverse cross sectional view of the electrical lead of FIG. 5 taken along lines 6-6 of FIG. 5.
Figure 7:
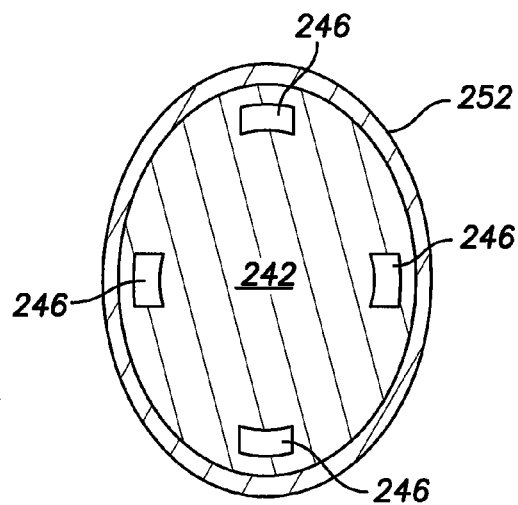
FIG. 7 is a transverse cross sectional view of the electrical lead of FIG. 5 taken along lines 7-7 of FIG. 5.
Figure 8:
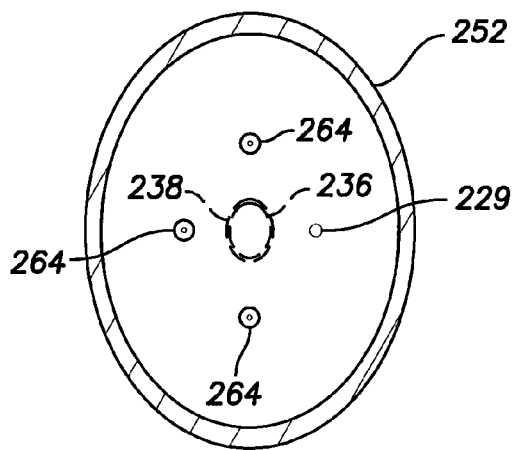
FIG. 8 is a transverse cross sectional view of the electrical lead of FIG. 5 taken along lines 8-8 of FIG. 5.
Figure 9:
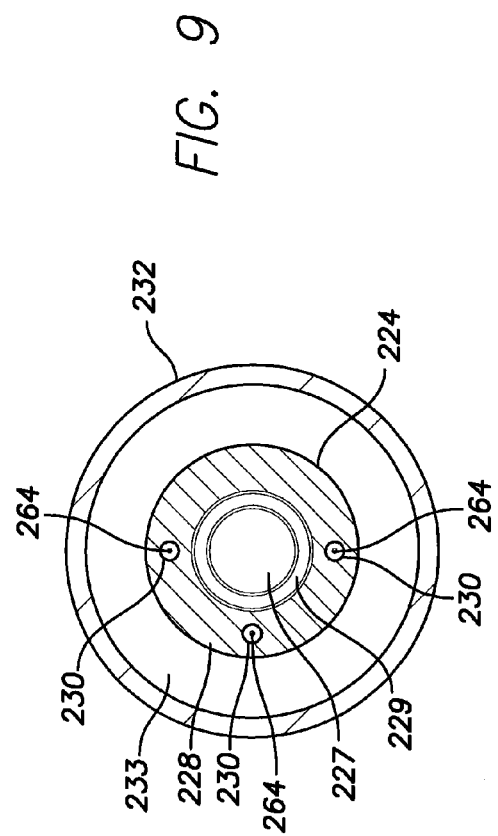
FIG. 9 is a transverse cross sectional view of the electrical lead of FIG. 5 taken along lines 9-9 of FIG. 5.

Referring to FIG. 4, the electrical lead 202 includes the elongate flexible lead body 204 having the proximal end 206, distal end 208 and a longitudinal axis 216 extending in an axial direction along a length of the elongate lead body 204. A proximal annular electrode 218 is disposed on a distal portion 220 of the lead body 204 proximal of the header assembly 214. The proximal annular electrode 218 is in electrical communication with electrical terminal 222 of proximal connector 210. Referring to FIGS. 5-9, the elongate lead body 204 includes a multi-lumen inner shaft 224 having a main inner lumen 226 extending along an axial direction of the inner shaft 224 and a wall portion 228 having a plurality of secondary lumens 230 extending along an axial direction of the inner shaft 224. An outer tubular shaft 232 has an inner lumen 233 that is disposed about and substantially concentric with the inner shaft 224. A tubular liner 225 is disposed within the main inner lumen 226 of the inner shaft 224 and has an inner lumen 227 that surrounds an outer surface of the threaded actuator member 238. An inner coil member 229 is disposed between an outer surface of the tubular liner 225 and an inside surface of the main inner lumen 226 of the inner shaft 224. The inner coil member 229 may be conductive or non-conductive and may be monofilar or multifilar. Typically, the inner coil member 229 will be a conductive multifilar coil that electrically couples one of the electrodes in the form of the tissue engaging members 246 with a conductive terminal on the proximal connector 210.

A bulkhead member 234 is secured to a distal end of a distal portion of the outer tubular shaft 232. The bulkhead member 234 includes a threaded lumen 236 having a longitudinal axis substantially aligned in an axial orientation parallel to the longitudinal axis 216 of the elongate lead body 204. An elongate threaded actuator member 238 is threadingly engaged with the threaded lumen 236 of the bulkhead member 234 and has a proximal coupling in the form of a socket 240 configured to allow torque transfer from an elongate member, such as stylet 242 shown in FIG. 12, engaged therewith. An enlarged distal end 243 of the threaded actuator member 238 is disposed within and captured by a cavity in an axially translatable tissue engaging member carrier 244. Such a configuration allows the threaded actuator member 238 to be rotated but still apply axial force in both a proximal and distal direction onto the carrier 244 relative to the bulkhead member 234 and outer shaft 232.

Four leaf shaped resilient tissue engaging members 246 are disposed at the distal end of the lead body 204 each having a proximal end 248 secured to the axially translatable carrier member 244. Each tissue engaging member 246 includes a sharpened distal end 250 configured to penetrate target tissue. Each tissue engaging member embodiment 246 is optionally made from a conductive material, such as a resilient metal, so as to form an electrode capable of making an electrical coupling with tissue in contact with the tissue engaging member 246. The resilient tissue engaging members 246 are oriented in a substantially axial orientation and are substantially axially coextensive with each other while in the radially retracted state shown in FIG. 5. The tissue engaging members 246 are configured to be radially extended by an axial displacement mechanism or other means in a controllable manner from the radially retracted state to a radially extended state with the sharpened distal ends 250 extending radially outwardly and distally from the lead body 204. The controllable distal and radial outward extension of the tissue engaging members 246 is configured so as to engage target tissue disposed adjacent to and distal of the distal end of the lead 202 as shown in FIGS. 14-16A discussed below.

For the embodiment shown, the axial displacement mechanism includes the axially translatable carrier member 244, the bulkhead member 234 and the threaded actuator member 238. However, other axial displacement mechanism embodiments may also be used. For some embodiments, the threaded actuator member 238 may made without threads and be configured to slide freely in the aperture 236, whether threaded or not, of the bulkhead member 234. For such embodiments, a stylet without any torque transfer surface may merely be pushed into a proximal coupling the threaded actuator member 238 in order to transmit axial force in a distal direction against the proximal surface of the carrier member 244. In addition, the threaded actuator member 238 could be eliminated and a stylet advanced through the aperture 236 of the bulkhead member 234 to directly apply axial force to the carrier member 244 and thus the tissue engaging members 246. For such an embodiment, controllable retraction of the tissue engaging members 246 by use of the stylet would not be possible.

The tissue engaging members 246 may be made from a variety of high strength resilient materials that may be either conductive or non-conductive. Materials such as stainless steel, MP35N, superelastic alloys such as nickel titanium alloys and the like may be used. For materials such as nickel titanium alloy that are less conductive that other alloys, a conductive coating such as gold, platinum or the like may be added. Such coatings may also be used to provide enhanced radiopacity to the tissue engaging members in order to facilitate imaging at deployment. The tissue engaging members 246 or electrodes on the tissue engaging members 246 may also be coated with a low polarization coating such as nitride, carbide or carbonitride (not shown). It may also be useful to coat the tissue engaging members 246, or portions of the electrical lead 202 adjacent the tissue engaging members 246, with a steroidal anti-inflammatory coating (not shown) such as dexamethasone which may serve to reduce a stimulation threshold by reducing or minimizing fibrotic encapsulation or fibrosis. Such a steroidal coating may be applied by dipping, spraying or any other suitable method. The tissue engaging member embodiments 246 shown are coated with a porous layer of titanium nitride and steroidal anti-inflammatory coating (not shown). In addition to coatings to provide enhanced imaging and electrical properties, the tissue engaging members 246, or portions thereof, may also be coated with materials to enhance the mechanical properties. Low friction materials such as flouropolymers, specifically, Teflon®, may be used as an outer coating on the tissue engaging members 246, or portions thereof, to reduce the frictional resistance of the tissue engaging members 246 during deployment. The tissue engaging members may have an axial length of about 1 mm to about 10 mm.

A tubular header 252 is disposed at the distal end of the lead body 204 and is axially displaceable relative to the tissue engaging members 246 by virtue of the ability of the carrier member 244 and the tissue engaging members 246 secured thereto to axially translate within an inner lumen of the header 252. The header 252 has a wall portion 254 with an inner surface 256 disposed about and radially constraining the tissue engaging members 246 while the tissue engaging members 246 are in the radially restrained state. The inner surface 256 may be made from a material which is sufficiently hard and lubricious to prevent the sharpened distal ends 250 of the tissue engaging members 246 from digging into the material of the header 252 while the tissue engaging members 246 are being axially advanced.

The header 252 also has a plurality of radially oriented apertures 258 in the wall portion 254 corresponding to, and axially aligned with, each resilient tissue engaging member 246 and configured to allow each respective tissue engaging member 246 to extend from the radially oriented aperture 258 upon axial translation in a distal direction relative to the header 252 of the tissue engaging members 246 from the radially constrained state. A steroid plug 260 is disposed at a distal end 262 of the header 252 and configured to contact target tissue upon deployment of the electrical lead 202 adjacent target tissue. The steroid plug 260 contains a steroidal anti-inflammatory drug, such as dexamethasone, or a material configured to elute a steroidal anti-inflammatory over time, that will reduce or prevent fibrosis or fibrotic encapsulation and the concomitant increase in stimulation threshold for the affected tissue. A plurality of conductor cables 264 are in electrical communication between respective electrodes in the form of the tissue engaging members 246 and conductive terminals of the connector 210.

Like the tissue engaging members 246, the header 252 may be made from a variety of high strength resilient materials that may be either conductive or non-conductive. Materials such as stainless steel, MP35N, nickel titanium alloys and the like may be used. For materials such as nickel titanium alloy that are less conductive that other alloys, a conductive coating such as gold, platinum or the like may be added if the header 252, or a distal portion thereof, is to be used as an electrode. Such coatings may also be used to provide enhanced radiopacity of the header 252 in order to facilitate imaging at deployment. If the header 252 is to be used as an electrode, the header 252 may also be coated with a low polarization coating such as nitride, carbide or carbonitride (not shown). In addition to coatings to provide enhanced imaging and electrical properties, the header 252, and particularly the radially oriented apertures 258 of the header 252, may also be coated with materials to enhance the mechanical properties. Low friction materials such as flouropolymers, specifically, Teflon®, may be used to reduce the frictional resistance of the tissue engaging members 246 during deployment through the radially oriented apertures 258. The header 252 may have an axial length of about 3 mm to about 20 mm and a transverse dimension or diameter of about 0.5 mm to about 5 mm.

Figure 10:
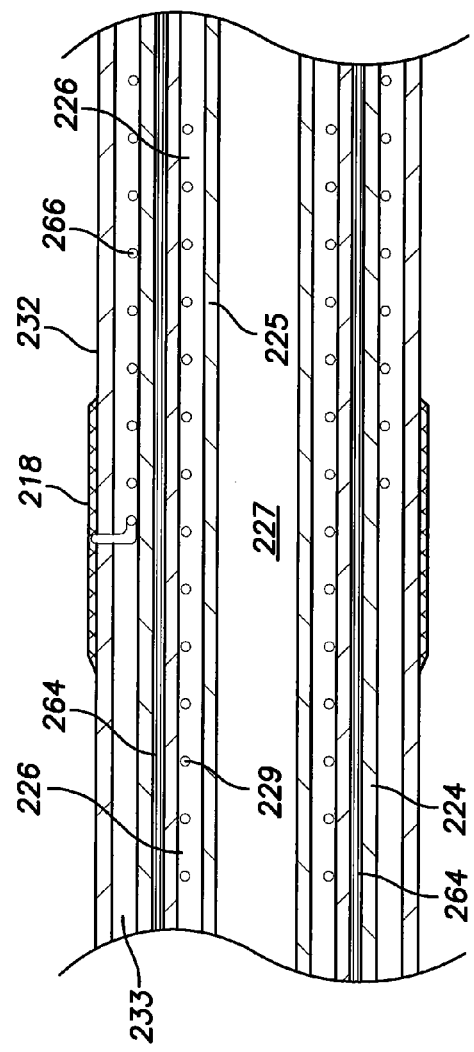
FIG. 10 is an enlarged view in section of the encircled portion of the electrical lead shown as 10-10 in FIG. 4.
Figure 11:
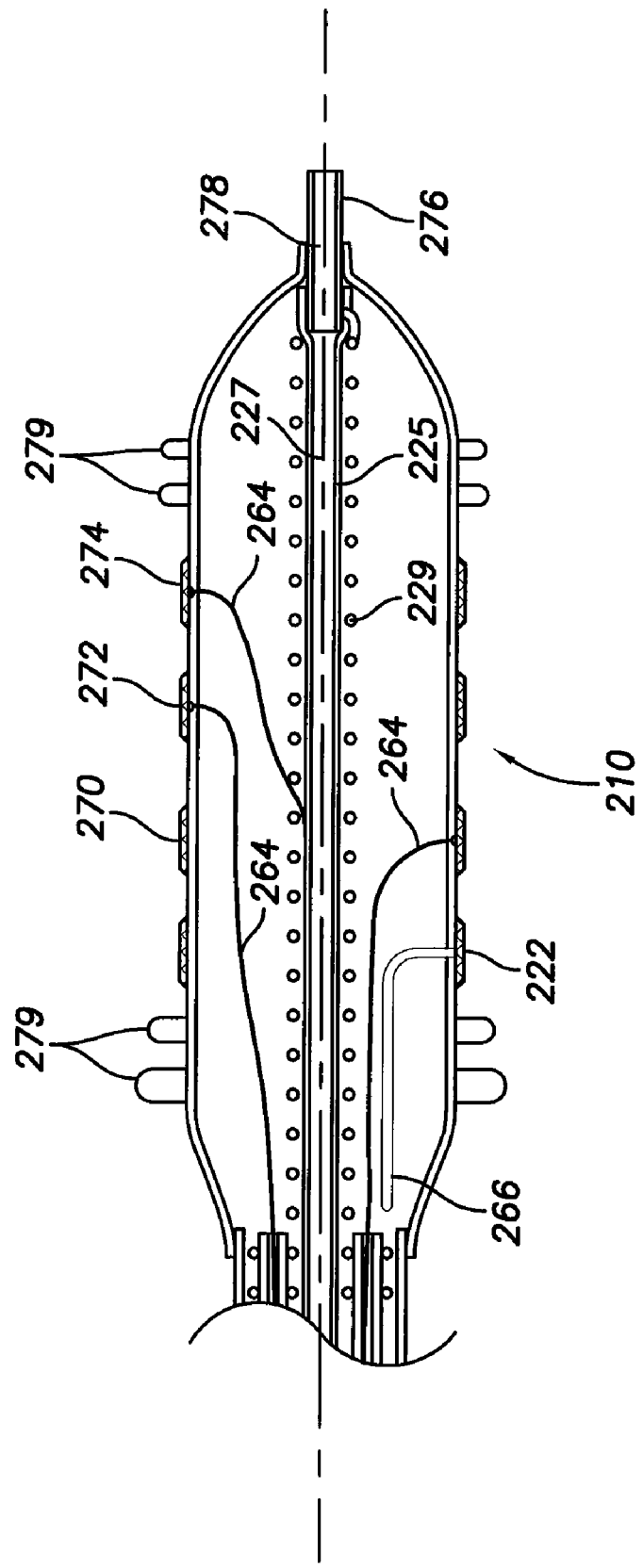
FIG. 11 is an enlarged view in section of the encircled portion of the electrical lead shown as 11-11 in FIG. 4 which illustrates an embodiment of a connector.

Referring to FIG. 10, the proximal annular electrode 218 is shown in more detail. An outer coil member 266 is electrically coupled to the proximal annular electrode 218 and a conductive terminal of the proximal connector 210. The outer coil member 266 is disposed within the inner lumen 233 of the outer shaft 232 between an outer surface of the inner shaft 224 and an inside surface of the inner lumen 233 of the outer shaft 232. The outer coil member 266 may be monofilar or multifilar. FIG. 11 shows connector 210 in section with conductive cables 264 electrically coupling electrodes to annular conductive terminals 270, 272 and 274. The inner coil member 229 is electrically coupled to the proximal tubular terminal 276. The proximal tubular terminal 276 has an inner lumen 278 in fluid communication with the inner lumen 227 of the tubular liner 225. The connector 210 includes several annular seals 279 that are configured to sealingly mate to an inside surface of the receptacle 212 of the stimulation device 10 or similar devices.

Referring to FIGS. 12-13C, the stylet 242 has an elongate shaft portion 280 disposed between a proximal handle portion 282 and a distal coupling portion 284. The proximal handle portion 282 may have a grip enhancing surface such as a knurled or rubber-like surface in order to facilitate rotation of the stylet 242. The distal coupling portion 284 may have a variety of configurations for coupling to the socket 240 of the threaded actuator member 238. The coupling between the distal coupling portion 284 and the socket 240 must transfer torque and rotation from the stylet shaft 280 to the threaded actuator member 238. FIGS. 13A-13C show several embodiments for the distal coupling portion 284 in transverse cross section. FIG. 13A shows a slotted or keyed embodiment wherein a slot 286 is configured to mate with a corresponding key in the socket 240. FIG. 13B shows a splined embodiment wherein an outside surface of the distal coupling portion has a plurality of splines 288 configured to mate with splines on an inside surface of the socket 240. FIG. 13C is a threaded embodiment having an outside surface with threads configured to mate with threads on an inside surface of socket 240. For each of these embodiments, the distal coupling portion 284 may be coupled to the socket 240 in a torque transmitting arrangement. After the desired rotation has been applied to the threaded actuator member 238, the distal coupling portion 284 may then be disengaged and withdrawn from the socket 240 and lumen 227.

FIGS. 14-16A show a deployment sequence of electrical lead embodiment 202 wherein the tissue engaging members 246 are radially extended in a controllable manner from a radially retracted state to a radially extended state. Initially, the implantable electrical lead 202 is advanced within a patient's body until a distal portion of the electrical lead 202 is disposed adjacent target tissue 290 of the patient's body as shown in FIG. 14. The target tissue 290 may include any tissue to which it may be desirable to deliver a stimulation signal or from which it may be desirable to receive or sense a signal. Tissue such as endocardial tissue of a patient's heart or the like may be suitable target tissue for some embodiments of the electrical lead 202. In FIG. 14, a distal end of the header 252 is disposed adjacent and in contact with target tissue 290 of the patient. At this point, the axial displacement mechanism may be activated. For the lead embodiment 202 shown, the stylet 242 may be advanced through the inner lumen 227 of the tubular liner 225 until the distal end of the stylet 242 engages the proximal coupling socket 240 of the threaded actuator member 238. The stylet 242 is then rotated from a proximal end thereof so as to rotate the threaded actuator member 238. Rotation of the threaded actuator member 238 axially displaces the distal end 243 of the threaded actuator member 238 in a controllable manner based on the number of rotations of the stylet and, thus, the carrier member 244 and tissue engaging members 246 secured thereto are also controllably advanced.

Figure 16A:
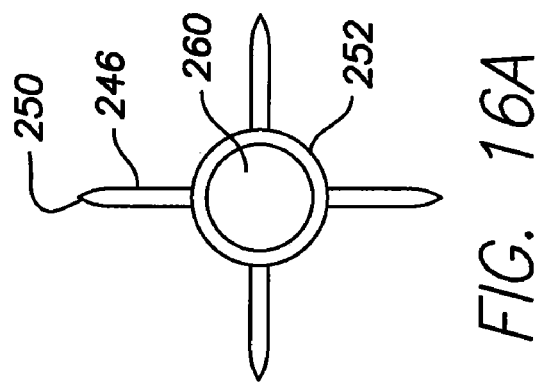
FIG. 16A is an end view of the electrical lead of FIG. 16 with the tissue engaging members in a fully radially extended state.
Figure 16:
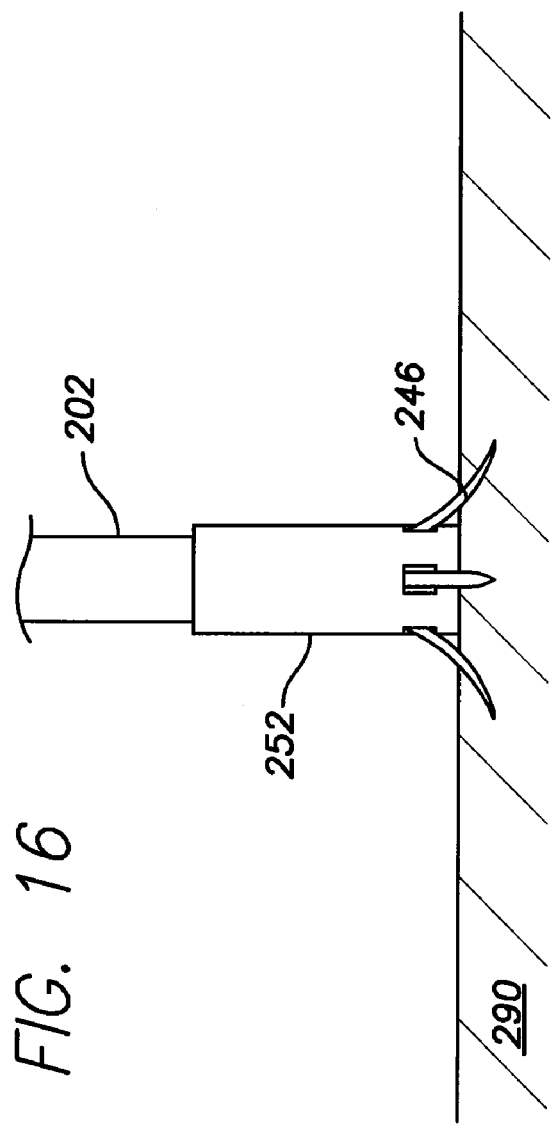
FIG. 16 is a side view of the distal portion of the electrical lead of FIG. 14 with the tissue engaging members penetrating the target tissue.

The tissue engaging members 246 are controllably deployed from the distal portion of the electrical lead 202 from a retracted state to a radially extended state wherein the tissue engaging members are disposed radially outward and distally forward so as to engage the target tissue 290 and secure the distal portion of the lead 202 to the target tissue 290. Radial extension of tissue engaging members 246 is continued until the tissue engaging members 246 are in a completely radially extended state as shown in FIG. 16. In the fully radially extended state, the sharpened distal ends 250 of the tissue engaging members 246 are extending radially outwardly and distally from the axially oriented apertures 258 of the header of the lead 202 so as to penetrate target tissue 290. The controllable distal and radial outward extension of the tissue engaging members 246 is configured so as to engage target tissue 290 disposed adjacent to and distal of the distal end of the header 252 and mechanically capture and secure the distal portion of the lead 202 to target tissue 290.

After achieving tissue engagement, a completely radially extended state, or any desirable position in between, an electrical signal may then be conducted through an electrode on the distal portion of the implantable electrical lead 202. A variety of methods may be used to deliver a therapeutic electrical signal to the target tissue. In some embodiments, a conductive path to each tissue engaging member electrode is sampled or otherwise tested for monopolar impedance, bipolar impedance or any other desirable electrical characteristic. Thereafter, an electrode or electrodes are selected for delivery of the therapeutic electrical signal with desirable impedance or clinical profile. For such embodiments, one or more of the electrodes may be used as a cathode and one or more of the electrodes as an anode of a signal to be delivered to target tissue. For some other embodiments, multiple electrodes may be electrically coupled together and used together as a single electrode or to deliver the same electrical signal to different contact points of target tissue of the patient.

Referring to FIGS. 17A-23, another embodiment of an electrical lead 302 is shown having a structure similar in many respects to the structure of electrical lead 202 discussed above. The electrical lead 302 includes the elongate flexible lead body 204 having a proximal end 206, distal end 208 and a longitudinal axis 216 extending in an axial direction along a length of the elongate lead body 204. A proximal annular electrode 218 is disposed on a distal portion 220 of the lead body 204 proximal of the header assembly 314. The proximal annular electrode 218 is in electrical communication with electrical terminal 222 of proximal connector 210. Referring to FIGS. 17B-23, the elongate lead body 204 includes a multi-lumen inner shaft 224 having a main inner lumen 226 extending along an axial direction of the inner shaft 224 and a wall portion 228 having a plurality of secondary lumens 230 extending along an axial direction of the inner shaft 224. An outer tubular shaft 232 is disposed about and substantially concentric with the inner shaft 224. A tubular liner 225 is disposed within the main inner lumen 226 of the inner shaft 224 and has an inner lumen 227 that surrounds an outer surface of the threaded actuator member 238. An inner coil member 229 is disposed between an outer surface of the tubular liner 225 and an inside surface of the main inner lumen 226 of the inner shaft 224. The inner coil member 229 may be conductive or non-conductive and may be monofilar or multifilar. Typically, the inner coil member 229 will be a conductive multifilar coil that electrically couples one of the electrodes in the form of the tissue engaging members 246 with a conductive terminal on the proximal connector 210.

A bulkhead member 234 is secured to a distal end of a distal portion of the outer tubular shaft 232. The bulkhead member 234 includes a threaded lumen 236 having a longitudinal axis substantially aligned in an axial orientation parallel to the longitudinal axis 216 of the elongate lead body 304. An elongate threaded actuator member 238 is threadingly engaged with the threaded lumen 236 of the bulkhead member 234 and has a proximal coupling in the form of a socket 240 configured to allow torque transfer from an elongate member, such as stylet 242 shown in FIG. 12 and discussed above, engaged therewith. An enlarged distal end 239 of the threaded actuator member 238 is disposed within and captured by a cavity in an axially translatable member 344. Such a configuration allows the threaded actuator member 238 to be rotated but still apply axial force in both a proximal and distal direction onto the axially translatable 344 relative to the bulkhead member 234 and outer shaft 232.

Figure 17A:
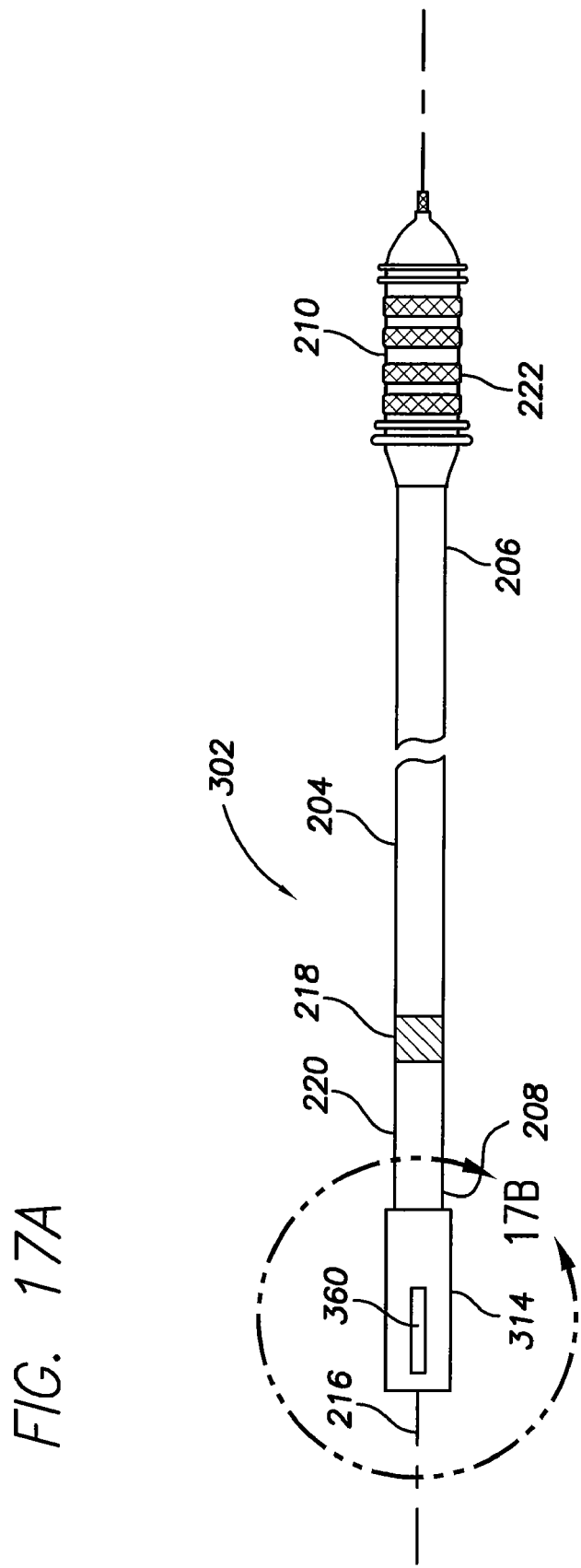
FIG. 17A is an elevational view of an embodiment of an electrical lead.
Figure 17B:
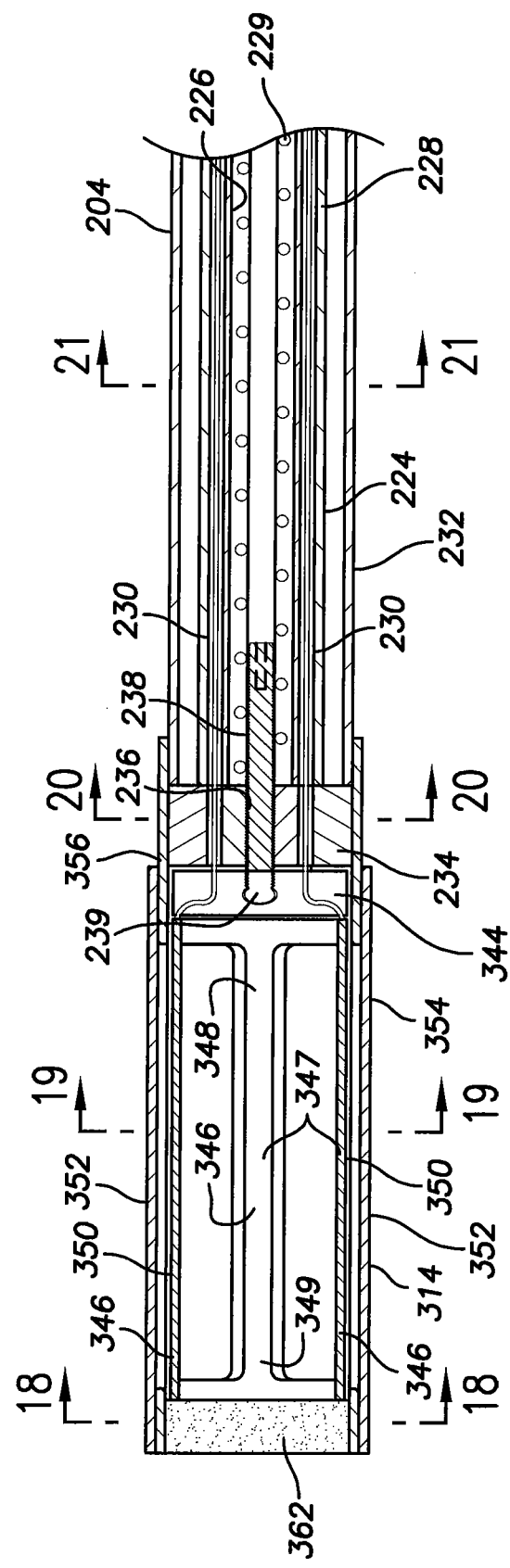
FIG. 17B is an enlarged view in partial section of a distal portion of an embodiment of an electrical lead indicated by the encircled portion 17B-17B in FIG. 17A.
Figure 19:
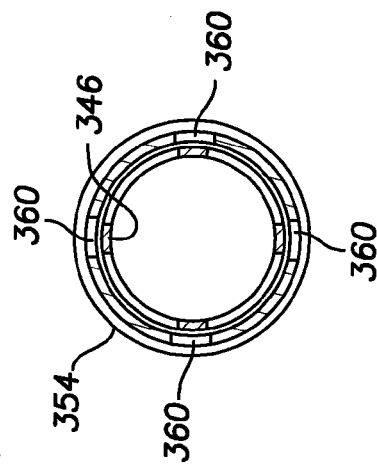
FIG. 19 is a transverse cross sectional view of the electrical lead of FIG. 17B taken along lines 19-19 of FIG. 17B.
Figure 21:
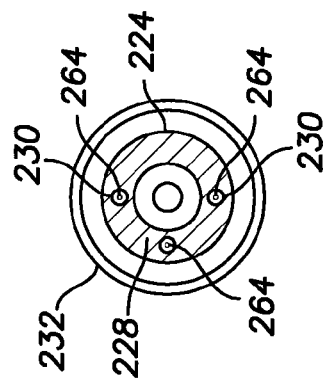
FIG. 21 is a transverse cross sectional view of the electrical lead of FIG. 17B taken along lines 21-21 of FIG. 17B.
Figure 18:
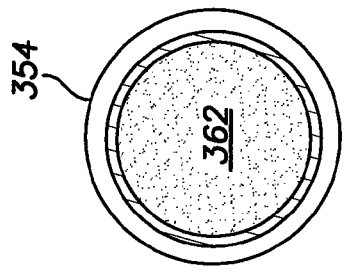
FIG. 18 is a transverse cross sectional view of the electrical lead of FIG. 17B taken along lines 18-18 of FIG. 17B.
Figure 20:
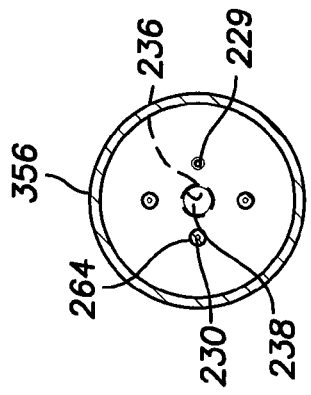
FIG. 20 is a transverse cross sectional view of the electrical lead of FIG. 17B taken along lines 20-20 of FIG. 17B.

A plurality of resilient tissue engaging members 346 disposed at the distal portion of the shaft and are configured to be radially extended in a controllable manner from a radially retracted state as shown in FIG. 17B to a radially extended state. Each tissue engaging member 346 has a proximal end 348 and a distal end 349 which are each radially constrained but axially moveable relative to each other. The tissue engaging members 346 are straight, substantially axially coextensive with each other and substantially aligned in an axial orientation with the longitudinal axis 216 of the body 204 in the radially retracted state. Each tissue engaging member 346 also has an intermediate portion 347 disposed between the proximal ends 348 and distal ends 349 that includes and electrode 350 which, for the embodiment shown in FIG. 17B, includes a portion of the tissue engaging members 346 which is both conductive and exposed through an aperture 352 in an expandable sheath 354 that is disposed about the header assembly 314. The expandable sheath 354 serves to seal and electrically insulate the header assembly 314, and particularly the elongate apertures 360 discussed below, from the ingress of body fluids or tissue ingrowth, that may adversely affect the electrical performance of the lead 302 by short circuiting the various electrodes or interfering with the mechanical performance. Portions of the expandable sheath 354 adjacent the tissue engaging members 346 need to radially and circumferentially expand during radial extension of the tissue engaging members 346. As such, the expandable sheath may be made from electrically insulating materials with a high elasticity, such as a low durometer silicone rubber or the like.

The intermediate portion 347 is deflected radially outward upon deployment of the tissue engaging members 346 to form a rounded tissue engaging portion by moving the respective proximal and distal ends 348 and 349 axially closer together so as to buckle or deform the tissue engaging member 346. Such radial outward deflection due to axial compression of the tissue engaging members 346 may be continued until the intermediate portions 347 of the tissue engaging members 346 engage surrounding target tissue without significant tissue penetration. The radial extension of the intermediate portion 347 which is rounded and substantially non-traumatic in the extended state allows the lead 302 to deliver and receive electrical signals from tissue without penetrating the target tissue. This, in turn, allows the lead 302 to be used at target tissue sites where perforation may be problematic. Target tissue sites including the coronary veins, coronary sinus and pericardial space may be suitable for some embodiments of electrical lead 302. The tissue engaging members 346 are configured to be radially extended with an axial displacement mechanism or other means in a controllable manner from the radially retracted state to a radially extended state with the intermediate portion 347 extending radially outwardly from the longitudinal axis 216 of the lead body 204 so as to engage target tissue disposed adjacent to the distal end of the header assembly 314 as shown in FIGS. 24-29 discussed below. Each tissue engaging member 346 is also optionally made from a conductive material, such as a resilient metal, so as to form an electrode capable of making an electrical coupling with tissue in contact with the tissue engaging member 346.

For the embodiment shown, the axial displacement mechanism includes the axially translatable member 344, the bulkhead member 234 and the threaded actuator member 238. However, other axial displacement mechanism embodiments may also be used. For some embodiments, the threaded actuator member 238 may made without threads and be configured to slide freely in the aperture 236, whether threaded or not, of the bulkhead member 234. For such embodiments, a stylet without any torque transfer surface may merely be pushed into a proximal coupling the threaded actuator member 238 in order to transmit axial force in a distal direction against the proximal surface of the carrier member 244. In addition, the threaded actuator member 238 could be eliminated and a stylet advanced through the aperture 236 of the bulkhead member 234 to directly apply a compressive axial force to the axially translatable member 344 and thus the tissue engaging members 346. For such an embodiment, controllable retraction of the tissue engaging members 346 by use of the stylet may still be possible depending on the elasticity of the particular tissue engaging member embodiments 346.

The tissue engaging members 346 may be made from a variety of high strength resilient materials that may be either conductive or non-conductive. Materials such as stainless steel, MP35N, nickel titanium alloys and the like may be used. For materials such as nickel titanium alloy that are less conductive that other alloys, a conductive coating such as gold, platinum or the like may be added. Such coatings may also be used to provide enhanced radiopacity to the tissue engaging members in order to facilitate imaging at deployment. The tissue engaging members 346 or electrodes 350 on the tissue engaging members 346 may also be coated with a low polarization coating such as nitride, carbide or carbonitride (not shown). It may also be useful to coat the tissue engaging members 346, electrodes 350 on the tissue engaging members 346, or portions of the electrical lead 302 adjacent the tissue engaging members 346, with a steroidal anti-inflammatory coating (not shown) such as dexamethasone which may serve to reduce a stimulation threshold by reducing or minimizing fibrotic encapsulation or fibrosis. Such a steroidal coating may be applied by dipping, spraying or any other suitable method. For the lead embodiment 302 shown, the expandable sheath 354 may be coated with an anti-inflammatory steroidal coating, particularly adjacent the apertures 352 from which portions of the tissue engaging members 346 protrude. In addition, the expandable sheath 354 may also be made from or include a drug eluting material that would serve to elute a steroidal anti-inflammatory drug over time. The tissue engaging member embodiments 346 shown are coated with a porous layer of titanium nitride and steroidal anti-inflammatory coating (not shown). In addition to coatings to provide enhanced imaging and electrical properties, the tissue engaging members 346, or portions thereof, may also be coated with materials to enhance the mechanical properties. Low friction materials such as flouropolymers, specifically, Teflon®, may be used as an outer coating on the tissue engaging members 346, or portions thereof, to reduce the frictional resistance of the tissue engaging members 346 during deployment. The tissue engaging members may have an axial length of about 1 mm to about 10 mm.

A tubular header 356 having a side wall 358 is disposed about an inner lumen of the header 356. An elongate aperture 360 corresponding and disposed radially adjacent to each tissue engaging member 346 in the side wall 358 of the header 356 allows the intermediate portion 347 of each tissue engaging member 346 to extend in a radial direction beyond the header 356 in a radially extended state. The elongated radially oriented apertures 360 extend axially in the wall portion 358 corresponding to, and axially aligned with, each resilient tissue engaging member 346 and configured to allow each respective tissue engaging member 346 to extend from the radially oriented aperture 360 upon axial compression and buckling of the tissue engaging members 346 from the radially retracted state.

Like the tissue engaging members 346, the header 356 may be made from a variety of high strength resilient materials that may be either conductive or non-conductive. Materials such as stainless steel, MP35N, nickel titanium alloys and the like may be used. For materials such as nickel titanium alloy that are less conductive that other alloys, a conductive coating such as gold, platinum or the like may be added if the header 356, or a distal portion thereof, is to be used as an electrode. Such coatings may also be used to provide enhanced radiopacity of the header 356 in order to facilitate imaging at deployment. If the header 356 is to be used as an electrode, the header 356 may also be coated with a low polarization coating such as nitride, carbide or carbonitride (not shown). In addition to coatings to provide enhanced imaging and electrical properties, the header 356, and particularly the radially oriented apertures 360 of the header 356, may also be coated with materials to enhance the mechanical properties. Low friction materials such as flouropolymers, specifically, Teflon®, may be used to reduce the frictional resistance of the tissue engaging members 246 during deployment through the radially oriented apertures 360. The header 356 may have an axial length of about 3 mm to about 20 mm and a transverse dimension or diameter of about 0.5 mm to about 5 mm.

An optional steroid plug 362 is disposed at a distal end 362 of the header 356 and configured to contact target tissue upon deployment of the electrical lead 302 adjacent target tissue. The steroid plug 362 contains a steroidal anti-inflammatory drug, such as dexamethasone, or a material configured to elute a steroidal anti-inflammatory over time, that will reduce or prevent fibrosis or fibrotic encapsulation and the concomitant increase in stimulation threshold for the affected tissue. Such a steroid plug 362 may be particularly useful in embodiments wherein the header 356, or a portion thereof, will be used as an electrode. For other embodiments, the steroid plug material may be disposed adjacent the tissue engaging members 346. A plurality of conductor cables 264 are in electrical communication between respective electrodes in the form of the exposed portions of conductive tissue engaging members 346 and conductive terminals of the connector 210.

FIG. 22 is an exploded view of a tissue engaging member assembly 370 having a proximal hoop 372 and a distal hoop 374 with the tissue engaging members 346 secured to and disposed between the proximal and distal hoops in an axial orientation. The tissue engaging member assembly 370 is disposed within the header 356 with each tissue engaging member aligned with a respective elongate aperture 360 of the header 356. In this embodiment, the tissue engaging members 346 are formed from a conductive material such as a metal and have a coating 376 of an insulative material such as a silicone or the like. The electrodes 350 are formed at exposed portions of the tissue engaging members where the coating 376 has been removed as shown in FIG. 23.

Figure 33:
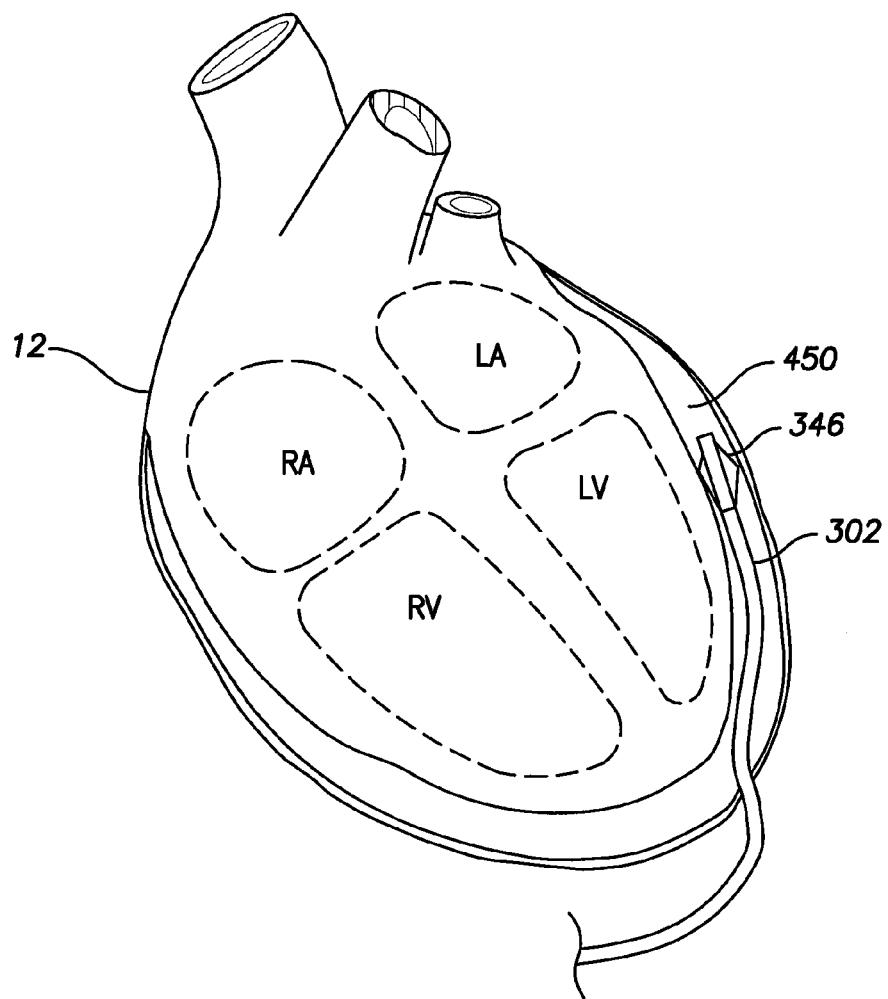
FIG. 33 is a sectional view of a patient's heart showing an embodiment of an electrical lead disposed in a pericardial space thereof.

FIGS. 24-29 show a deployment sequence of electrical lead embodiment 302 wherein the tissue engaging members 346 are radially extended in a controllable manner from a radially retracted state to a radially extended state. For the embodiment shown, the electrical lead 302 is deployed within a lumen 380 of the patient's body, such as a coronary vein, however, a similar method may be used to deploy the lead 302 within any suitable body space where tissue engaging members 346 will engage tissue. For example, the electrical lead 302 may be deployed within the pericardial space of a patient between epicardial tissue of the patient's heart 12 and the pericardial sac, as shown in FIG. 33 and discussed below.

Referring again to FIGS. 24-29, the implantable electrical lead 302 is advanced within a patient's body lumen 380 until a distal portion of the electrical lead 302 is disposed adjacent target tissue of the patient's body lumen 380 as shown in FIGS. 24 and 25. At this point, the axial displacement mechanism may be activated. For the lead embodiment 302 shown, the stylet 242 may be advanced through the inner lumen 227 of the tubular liner 225 until the distal end of the stylet 242 engages the proximal coupling 240 of the threaded actuator member 238. The stylet 242 is then rotated from a proximal end thereof so as to rotate the threaded actuator member 238. Rotation of the threaded actuator member 238 axially displaces the distal end of the threaded actuator member 238 in a controllable manner based on the number of rotations of the stylet 242 and, thus, the carrier member 344. Axial displacement of the carrier member 344 serves to axially compress the tissue engaging members 346 mechanically coupled thereto so as to buckle the tissue engaging members. The intermediate portion 347 of each tissue engaging member 346 is deflected radially outward upon deployment of the tissue engaging members 346 by moving the respective proximal and distal ends 348 and 349 axially closer together so as to buckle or deform the tissue engaging member 346 as shown in FIGS. 26 and 27. Portions of the expandable sheath 354 adjacent the tissue engaging members 346, and particularly the intermediate portion 347 of the tissue engaging members 346, are also radially expanded during this process as shown. The expandable sheath 354 is illustrated in FIGS. 24-29 as a thin transparent sheath that allows visualization of the header assembly 314 there through.

Figure 29:
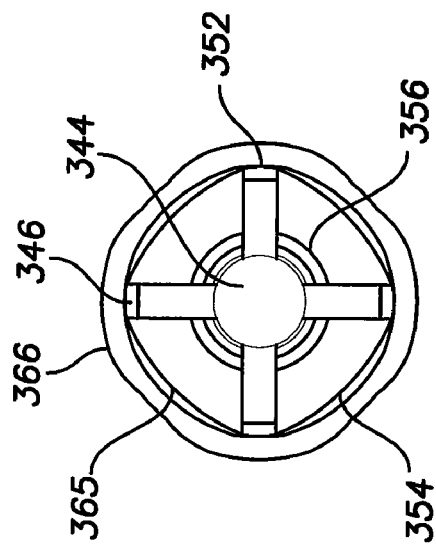
FIG. 29 is a transverse cross sectional view of the electrical lead of FIG. 28 taken along lines 29-29 of FIG. 28.
Figure 28:
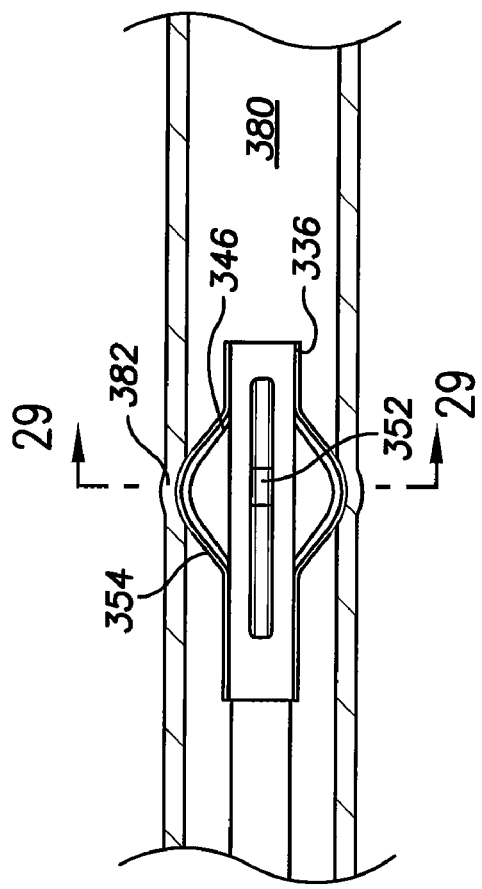
FIG. 28 shows the lead of FIG. 24 with the tissue engaging members in a radially extended state and engaging target tissue on an inside surface of the body lumen.

The tissue engaging members 346 are controllably deployed from the distal portion of the electrical lead 302 from a retracted state to an axially extended state to as to engage the target tissue 382. Such radial outward deflection and extension due to axial compression of the tissue engaging members 346 may be continued until the intermediate portion 347 of the tissue engaging members 346 fully engage surrounding target tissue 382 as shown in FIGS. 28 and 29. In the fully radially extended state, the intermediate portions 347 form apices that protrude through apertures 352 of the expandable sheath 354 and directly engage target tissue 382 disposed adjacent to the header 356.

After achieving tissue engagement, a completely radially extended state, or any desirable position in between, an electrical signal may then be conducted through an electrode 350 or any other electrode on the distal portion of the implantable electrical lead 302. A variety of methods may be used to deliver a therapeutic electrical signal to the target tissue. In some embodiments, a conductive path to each tissue engaging member electrode is sampled or otherwise tested for monopolar impedance, bipolar impedance or any other desirable electrical characteristic. Thereafter, an electrode or electrodes are selected for delivery of the therapeutic electrical signal with desirable impedance or clinical profile. For such embodiments, one or more of the electrodes may be used as a cathode and one or more of the electrodes as an anode of a signal to be delivered to target tissue. For some other embodiments, multiple electrodes may be electrically coupled together and used together as a single electrode or to deliver the same electrical signal to different contact points of target tissue of the patient.

Figure 30:
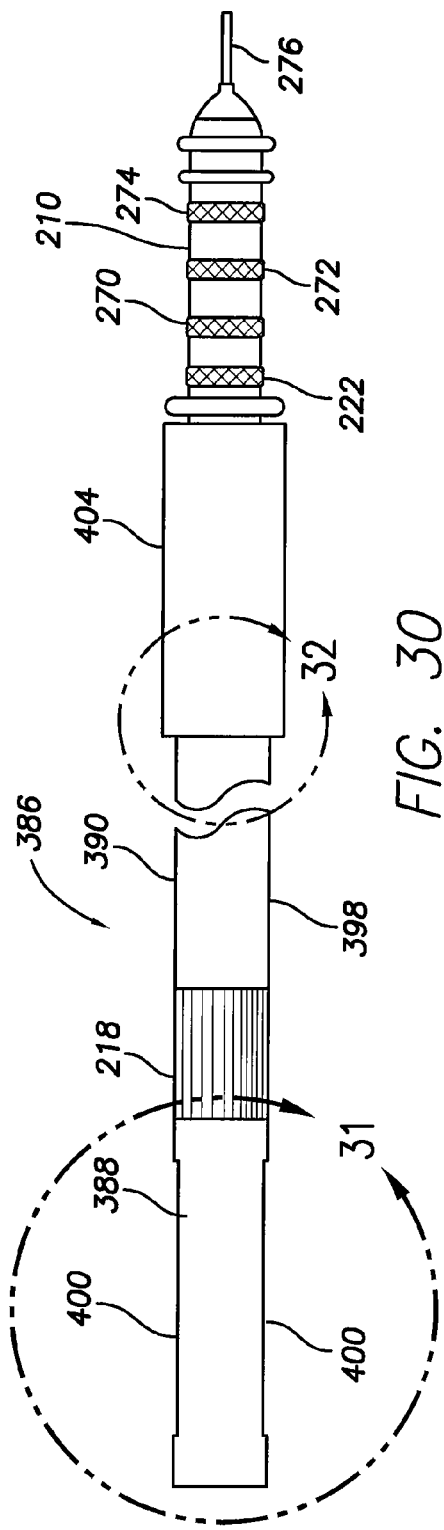
FIG. 30 is an elevational view of an embodiment of an electrical lead.
Figure 31:
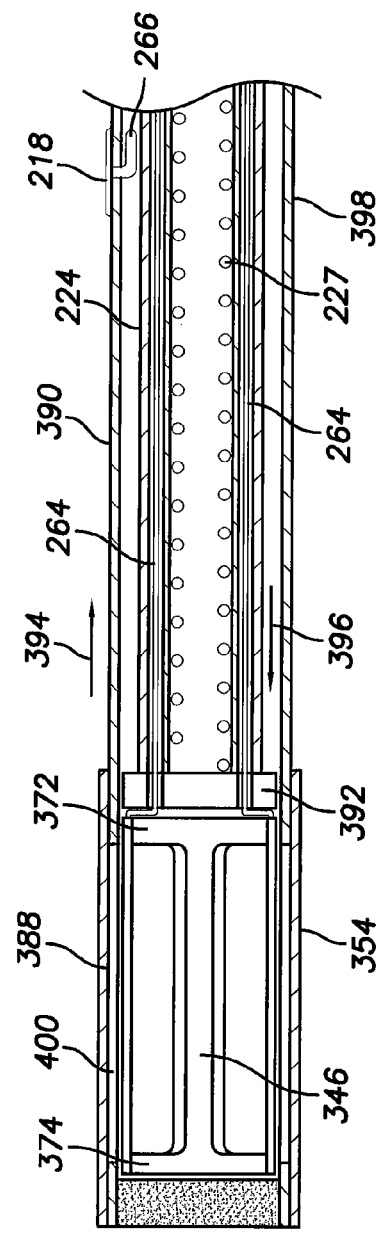
FIG. 31 is an enlarged view in partial section of the electrical lead of FIG. 30 indicated by the encircled portion 31-31 of FIG. 30.
Figure 32:
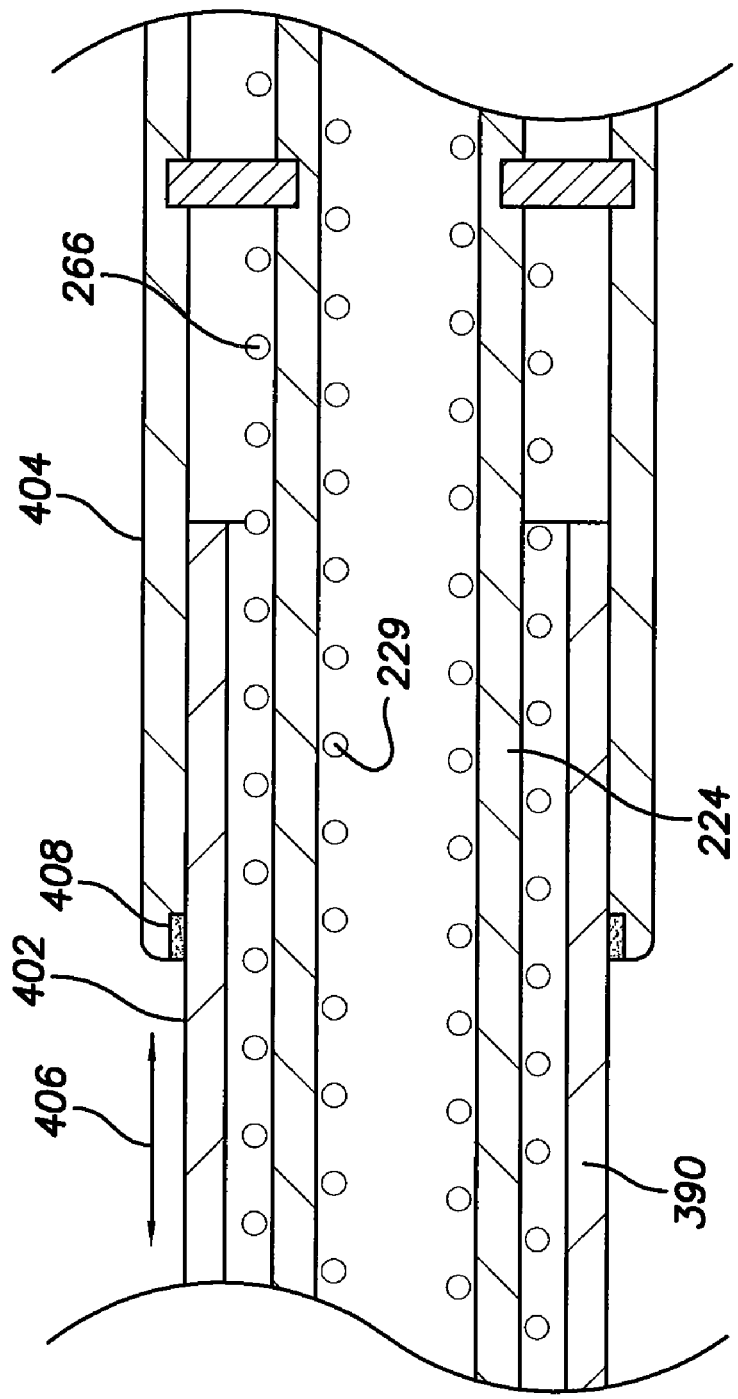
FIG. 32 is an enlarged view in partial section of the electrical lead of FIG. 30 indicated by the encircled portion 32-32 of FIG. 30.

FIGS. 30-32 illustrate an embodiment of an electrical lead 386 having a header configuration similar to that of electrical lead 302. As shown in the enlarged sectional view of FIG. 31, a header 388 is secured to or formed as part of the outer tubular shaft member 390. A distal end of a multiple lumen inner shaft member 224 is secured to a carrier member 392. Deployment of the tissue engaging members 346 with regard to radial extension from a radially retracted state is controlled by imparting relative axial movement between the outer tubular shaft 390 and the inner multiple lumen shaft 224 as shown by arrows 394 and 396, respectively. Imparting such relative axial movement between the outer tubular shaft 390 and the inner shaft 224 may be carried out manually by an operator of the lead, or by any other suitable means such as a screw drive mechanism (not shown) or the like. The relative axial translation of the outer shaft 390 and inner shaft 224 generates axial compression within the header 388 that compresses the tissue engaging members 346 so as to buckle them such that the intermediate portion 347 extends in an outward radial direction through elongate axial apertures 400 in the header 388. The proximal connector assembly 210 may be the same as or similar to the connector 210 discussed above. The header 388 may also include an expandable sheath 354 as discussed above.

The relative axial displacement between the outer tubular shaft 390 and inner shaft 224 is facilitated by a sealed sliding arrangement at the proximal end of an elongate lead body 398 of the electrical lead 386 as shown in the enlarged view of a proximal portion of the lead body 398 as shown in FIG. 32. A proximal end 402 of the outer tubular shaft 390 slides axially within an inner lumen of a proximal tubular member 404 as shown by arrow 406. An annular seal 408 is disposed at a distal end of the proximal tubular member 404 to seal the proximal tubular member with an outside surface of the outer tubular shaft 390. Locking pins 410 are disposed between inner shaft 224 and proximal tubular member 404 to prevent relative axial movement therebetween. Use of electrical lead 386 with regard to the interaction of the tissue engaging members 346 with target tissue 382 may be the same as or similar to the use and deployment of electrical lead 302 discussed above and illustrated in FIGS. 24-29. As discussed above, the radial extension of the tissue engaging members 346 of lead 386 is carried out by imparting relative axial movement or translation between the outer shaft 390 and inner shaft 224 instead of the stylet driven axial displacement mechanisms discussed above.

Referring to FIG. 33, electrical lead embodiments 302 and 386 having non-penetrating tissue engaging members 346, may be deployed to the pericardial space 450 of a patient's heart 12. FIG. 33 shows a distal portion of electrical lead 302 disposed within the pericardial space 450 of the patient's heart 12. Such deployment to the pericardial space 450 may serve to allow access to the left ventricle of a patient's heart 12 or many other desirable sites. Access to the pericardial space 450 may be achieved by a non-invasive subxiphoid approach with the use of a hollow needle, such as a Toughy needle, guidewire, dilator and introducer sheath (not shown). In such a procedure, the Toughy needle is advanced through the patient's chest to the pericardial space 450 of the patient's heart 12. Thereafter, the guidewire is advanced through an inner lumen of the needle until it is disposed within the pericardial space 450. The dilator and introducer sheath are then advanced over the guidewire such that a distal end of the introducer sheath is disposed within the pericardial space 450. The dilator and guidewire may then be withdrawn from the introducer sheath leaving the inner lumen of the introducer sheath positioned to function as an access canal from a location outside the patient's body to the pericardial space 450. The lead 302 may then be advanced through the inner lumen of the introducer sheath and positioned within the pericardial space 450.

In general, a wide variety of techniques can be implemented consistent with the principles the invention and no attempt is made herein to describe all possible techniques. Although described primarily with reference to embodiments wherein the implanted stimulation device is a defibrillation/pacer, the principles discussed herein are applicable to other implantable medical devices as well. The various functional components of the exemplary embodiments may be implemented using any appropriate technology including, for example, microprocessors running software programs or application specific integrated circuits (ASICs) executing hard-wired logic operations. With regard to the above detailed description, like reference numerals used therein refer to like elements that may have the same or similar dimensions, materials and configurations. While particular forms of embodiments have been illustrated and described, various modifications can be made without departing from the spirit and scope of the embodiments of the invention. Accordingly, it is not intended that the invention be limited by the forgoing detailed description.

What is claimed is:

1. An implantable electrical lead, comprising:
   an elongate flexible lead body having a distal portion;
   a plurality of substantially axially coextensive resilient tissue engaging members disposed at the distal portion of the lead body and configured to be controllably expandable from a retracted state to a radially extended state so as to engage adjacent target tissue, distal tips of the tissue engaging members being sharp and configured to penetrate the adjacent target tissue, and the plurality of tissue engaging members disposed radially outwardly and distally when in the radially extended state such that the distal tips of the tissue engaging member are oriented in a distal direction to penetrate the adjacent target tissue;
   an axial displacement mechanism mechanically coupled to the tissue engaging members;
   at least one electrode disposed at the distal portion of the lead body;
   a connector disposed at a proximal end of the lead body and having at least one conductive terminal; and
   at least one conductor cable in electrical communication between respective electrodes and conductive terminals of the connector.

2. The lead of claim 1 wherein at least one tissue engaging member comprises an electrode.

3. The lead of claim 2 wherein a plurality of the tissue engaging members comprise electrodes.

4. The lead of claim 2 wherein at least one of the tissue engaging members is made from a conductive material with an outer surface that functions as an electrode.

5. The lead of claim 1 wherein the at least one electrode includes a low polarization coating.

6. The lead of claim 1 wherein the at least one electrode comprises an annular electrode disposed on the lead body proximal of the tissue engaging members in a deployed radially extended state.

7. The lead of claim 1 further comprising a header with an outer cylindrical surface and radially oriented side apertures, the radially oriented side apertures disposed on a side surface of the outer cylindrical surface and configured to allow the tissue engaging members to extend therefrom.

8. The lead of claim 7 further comprising a steroid plug disposed on a distal end of the header.

9. The lead of claim 1 wherein the axial displacement mechanism comprises
   a bulkhead member having a threaded lumen disposed in an axial orientation secured to a distal portion of the lead body;
   a threaded actuator member threadingly engaged with the threaded lumen of the bulkhead having a distal end and a proximal coupling configured to allow torque transfer from an elongate member engaged therewith; and an axially translatable carrier member which is secured to a proximal end of each tissue engaging member and which has a proximal surface disposed adjacent the distal end of the threaded actuator member.

10. An implantable electrical lead, comprising:

an elongate flexible lead body;

an axial displacement mechanism disposed at a distal portion of the flexible lead body;

a plurality of resilient tissue engaging members disposed at a distal end of the lead body each having a sharpened distal tip configured to penetrate target tissue and an electrode, the resilient tissue engaging members oriented in an axial direction substantially axially coextensive with each other while in a radially retracted state and configured to be radially extended in a controllable manner from the radially retracted state to a radially extended state with the sharpened distal tips extending radially outwardly and distally from the lead body such that the distal tips are oriented in a distal direction so as to engage target tissue disposed adjacent to and distal of the distal end of the lead body;

a tubular header disposed at the distal end of the lead body which constrains the tissue engaging members while in the radially retracted state and which also has a radially oriented side aperture corresponding to each resilient tissue engaging member configured to allow each respective tissue engaging member to extend from the radially oriented side aperture upon deployment of the tissue engaging member from the radially constrained state;

a connector disposed at a proximal end of the shaft having a plurality of conductive terminals; and a plurality of conductor cables in electrical communication between respective electrodes and conductive terminals of the connector.

11. The lead of claim 10 wherein the electrodes include a low polarization coating.

12. The lead of claim 10 further comprising an annular electrode proximal of the tissue engaging members in a deployed radially extended state.

13. The lead of claim 10 wherein the lead comprises about 3 tissue engaging members to about 8 tissue engaging members.

14. The lead of claim 10 wherein the axial displacement mechanism comprises:

a bulkhead member having a threaded lumen disposed in an axial orientation secured to a distal portion of the lead body;

a threaded actuator member threadingly engaged with the threaded lumen of the bulkhead and having a proximal coupling and a distal end; and an axially translatable carrier member which has a proximal surface disposed adjacent the distal end of the threaded actuator member and which has proximal ends of the tissue engaging members secured thereto.

15. The lead of claim 10 further comprising a steroid plug disposed at a distal end of the header and configured to contact target tissue upon deployment of the electrical lead adjacent target tissue.

16. The lead of claim 10 further comprising a proximal annular electrode disposed proximally of the tissue engaging members on the elongate lead body.

* * * * *